(12) United States Patent
Mohamadzadeh

(10) Patent No.: US 8,372,409 B2
(45) Date of Patent: Feb. 12, 2013

(54) DENDRITIC CELL BINDING PROTEINS AND USES THEREOF

(75) Inventor: Mansour Mohamadzadeh, Frederick, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1470 days.

(21) Appl. No.: 10/552,153

(22) PCT Filed: Apr. 8, 2004

(86) PCT No.: PCT/US2004/010832
§ 371 (c)(1), (2), (4) Date: May 16, 2008

(87) PCT Pub. No.: WO2004/092195
PCT Pub. Date: Oct. 28, 2004

(65) Prior Publication Data
US 2010/0278857 A1    Nov. 4, 2010

Related U.S. Application Data

(60) Provisional application No. 60/461,474, filed on Apr. 9, 2003.

(51) Int. Cl.
| | | |
|---|---|---|
| A61K 39/295 | (2006.01) |
| A61K 39/145 | (2006.01) |
| A61K 39/21 | (2006.01) |
| A61K 39/15 | (2006.01) |
| A61K 39/12 | (2006.01) |
| A61K 39/00 | (2006.01) |

(52) U.S. Cl. ........... 424/202.1; 424/206.1; 424/207.1; 424/215.1; 424/218.1; 424/277.1

(58) Field of Classification Search .......... None
See application file for complete search history.

(56) References Cited

U.S. PATENT DOCUMENTS

| | | |
|---|---|---|
| 2002/0009430 A1 | 1/2002 | Lindhoffer et al. |
| 2002/0041864 A1 | 4/2002 | Fanslow et al. |
| 2002/0051780 A1 | 5/2002 | Lindhoffer et al. |
| 2002/0077276 A1 | 6/2002 | Fredeking et al. |
| 2002/0164582 A1 | 11/2002 | Hart et al. |
| 2002/0182222 A1 | 12/2002 | De Groot |
| 2005/0058657 A1 | 3/2005 | Ertl et al. |
| 2010/0278857 A1* | 11/2010 | Mohamadzadeh et al. .......... 424/202.1 |

FOREIGN PATENT DOCUMENTS
WO    WO 03/011334    2/2003

OTHER PUBLICATIONS

Oxenius and Bachmann. Similar Ligand Densities Required for Restimulation and Effector Function of Cytotoxic T Cells. Cellular Immunology. 1997; 179:16-21.*

Liljeqvist and Stahl. Production of recombinant subunit vaccines: protein immunogens, live delivery systems and nucleic acid vaccines. Journal of Biotechnology. 1999; 73(1): 1-33.*

McKinnon, et al. HIV Vaccine Efficacy Trials: A Brief History,and Options for Going Forward. AIDS Rev. 2010;12:209-17.*

(Continued)

*Primary Examiner* — Zachariah Lucas
*Assistant Examiner* — Stuart W Snyder
(74) *Attorney, Agent, or Firm* — Saliwanchik, Lloyd & Eisenschenk

(57) ABSTRACT

The present invention provides novel peptides which specifically targets and binds to dendritic cells. Also provided are fusion compositions comprising these peptides and a non-dendritic protein of fragments thereof. Further provided are DNA sequences encoding these peptides and fusion compositions. Methods of using the peptides or fusion compositions to promote an immune responses in an individual via administration also are provided.

12 Claims, 23 Drawing Sheets

DC-Peptide # 3         Control Peptide

OTHER PUBLICATIONS

Montagnier L. 25 years after HIV discovery: Prospects for cure and vaccine. Virology. 2010; 397: 248-254.*

Cohen J. Did Merck's Failed HIV Vaccine Cause Harm? Science. 2007; 318: 1048-1049.*

Rerks-Ngarm, et al. Vaccination with ALVAC and AIDSVAX to Prevent HIV-1 Infection in Thailand. New Eng. J. Med. 2009; 361(23): 2209-2220.*

Haynes, et al. Immune-Correlates Analysis of an HIV-1 Vaccine Efficacy Trial. New Engl J Med. 2012; 366(14): 1275-86.*

Steinman, R. et al. "Exploiting dendritic cells to improve vaccine efficacy" The *Journal of Clinical Investigation*, Jun. 2002, pp. 1519-1526, vol. 109.

Written Opinion in International Application No. PCT/US2004/10832, Mar. 3, 2005, pp. 1-3.

\* cited by examiner

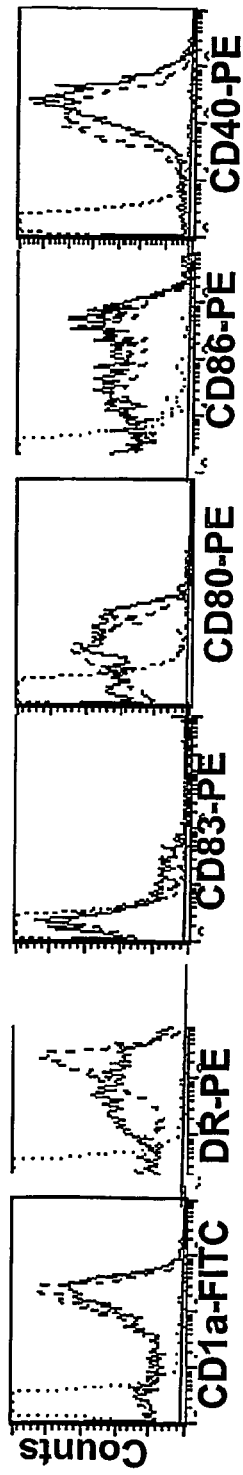
Fig. 3A
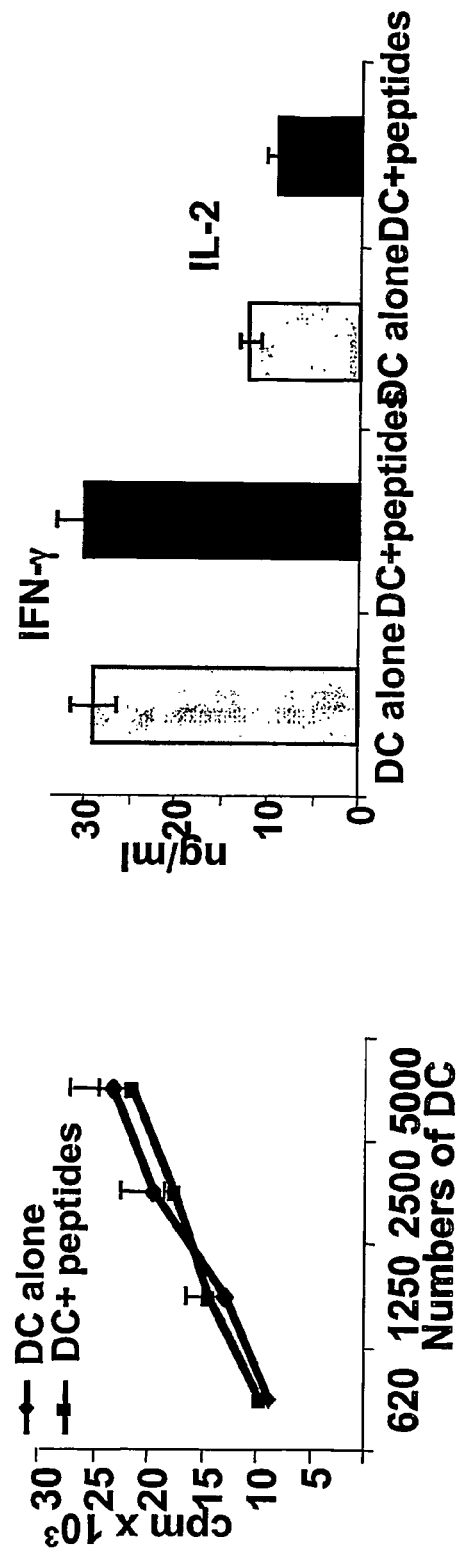
Fig. 3C
Fig. 3B

5'-
catgccatggagaagaagatctttggagcctggcattctgccgctttgatgggacctcgagggcggaggtCGTAG
ACTGCTGCAGGAAAC 3'    epitope 1                                              *
NcoI

Reverse primer:
5'-gccgggtacctggggtccctgccatgcgggagaa                                        *
ttcagacaccaactctccgccaccGCTAGGTGTCAGGGGCTCCAC 3'
                        epitope 3 (antisense)    Gly. hinge
KpnI Gly.hinge

Fig. 9A

SEQUENCE LISTING

```
<160> NUMBER OF SEQ ID NOS: 40

<210> SEQ ID NO 1
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 1

Tyr Pro Ile Val Asn Thr Ala Val Ala Thr His Met
                5                   10

<210> SEQ ID NO 2
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 2

Ala Thr Phe Thr Val Gly Pro Pro Gln Leu Leu Arg
                5                   10
```

```
<210> SEQ ID NO 3
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 3

Phe Tyr Pro Ser Tyr His Ser Thr Pro Gln Arg Pro
                5                   10

<210> SEQ ID NO 4
<211> LENGTH: 12
<212> TYPE: PRT
<213> ORGANISM: artificial sequence
<220> FEATURE:
<223> OTHER INFORMATION: peptide specific to myeloid dendritic cells
<220> FEATURE:
<221> NAME/KEY: MISC_FEATURE
<222> LOCATION: 7
<223> OTHER INFORMATION: Xaa is any amino acid

<400> SEQUENCE: 4

Thr Ser Ile Gly Thr His Xaa Leu Ser Ala Ala Leu
                5                   10

<210> SEQ ID NO 5
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 5

Thr Glu Thr Ser Trp Ser Met Phe Pro Leu His Leu
                5                   10

<210> SEQ ID NO 6
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 6

Ala Pro His Leu Pro Tyr Leu Arg Gly Leu Asn Leu
                5                   10

<210> SEQ ID NO 7
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 7

His His Asn Ser Asn His Arg Ser Phe His Tyr Leu
                5                   10

<210> SEQ ID NO 8
<211> LENGTH: 12
<212> TYPE: PRT
<213> ORGANISM: artificial sequence
<220> FEATURE:
<221> NAME/KEY: PEPTIDE
```

```
<223> OTHER INFORMATION: peptide specific to myeloid dendritic cells

<400> SEQUENCE: 8

Ser Tyr Ala Asn Leu Ile Arg Ser Ile Gln Pro Gly
                 5                  10

<210> SEQ ID NO 9
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 9

Thr Leu Val His Gln Trp Gln Pro Trp Pro Lys Ala
                 5                  10

<210> SEQ ID NO 10
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 10

Ile Arg His Thr Thr Ser Gly Pro Pro Pro Ser Ser
                 5                  10

<210> SEQ ID NO 11
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 11

Tyr Pro Gln Ala Leu Asn Thr Gln Pro Asp Trp Pro
                 5                  10

<210> SEQ ID NO 12
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 12

Ala Tyr Tyr Lys Thr Ala Ser Leu Ala Pro Ala Glu
                 5                  10

<210> SEQ ID NO 13
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 13

Ser Gln Asn Ser Leu Tyr Ser Ser Lys Pro Val Arg
                 5                  10

<210> SEQ ID NO 14
<211> LENGTH: 12
```

```
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 14

Ser Leu Ser Leu Leu Thr Met Pro Gly Asn Ala Ser
                5                   10

<210> SEQ ID NO 15
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 15

Gln Ser Gln Thr Tyr Gln Thr His Ser Val Thr Met
                5                   10

<210> SEQ ID NO 16
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 16

Glu Pro Ile His Pro Glu Thr Thr Phe Thr Asn Asn
                5                   10

<210> SEQ ID NO 17
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 17

Glu Thr Pro Met Val His Trp Pro Ser Thr Ser Pro
                5                   10

<210> SEQ ID NO 18
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 18

Ser Leu Ser Leu Leu Thr Met Pro Gly Asn Ala Ser
                5                   10

<210> SEQ ID NO 19
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 19

Asn Trp Trp Ser Asp Trp Val Met Leu Thr Gln Ser
                5                   10
```

```
<210> SEQ ID NO 20
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to myeloid dendritic cells

<400> SEQUENCE: 20

Gln Trp Pro Gln Tyr His Tyr Leu Arg Pro Thr Leu
                5                   10

<210> SEQ ID NO 21
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 21

Ser Ile Thr Gln His Leu Gln Leu Lys Pro Leu Ala
                5                   10

<210> SEQ ID NO 22
<211> LENGTH: 12
<212> TYPE: PRT
<213> ORGANISM: artificial sequence
<220> FEATURE:
<223> OTHER INFORMATION: peptide specific to Langerhans dendritic cells
<220> FEATURE:
<221> NAME/KEY: MISC_FEATURE
<222> LOCATION: 9
<223> OTHER INFORMATION: Xaa is any amino acid

<400> SEQUENCE: 22

Val Ser His Pro Leu Trp His Pro Xaa Arg Ile Leu
                5                   10

<210> SEQ ID NO 23
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 23

Val Ser Ser Pro Pro Arg Val Ser Gly Ile Gly Leu
                5                   10

<210> SEQ ID NO 24
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 24

His Pro Pro Glu Ile Tyr Ser Pro Pro Arg Tyr Pro
                5                   10

<210> SEQ ID NO 25
<211> LENGTH: 12
<212> TYPE: PRT
<213> ORGANISM: artificial sequence
<220> FEATURE:
```

```
<221> NAME/KEY: PEPTIDE
<223> OTHER INFORMATION: peptide specific to Langerhans dendritic cells

<400> SEQUENCE: 25

His Ser Leu Arg Leu Asp Phe Met Ala Pro Leu Thr
                5                   10

<210> SEQ ID NO 26
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 26

Leu Pro Pro Gly Ala Asp Leu Tyr Phe His Pro Ser
                5                   10

<210> SEQ ID NO 27
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 27

Ile Pro Pro Leu Arg Ile Thr Glu Val Thr Pro Thr
                5                   10

<210> SEQ ID NO 28
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 28

Ile Arg His Thr Thr Ser Gly Pro Pro Ser Ser
                5                   10

<210> SEQ ID NO 29
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 29

Val Ser Ser Pro Pro Arg Val Ser Gly Ile Gly Leu
                5                   10

<210> SEQ ID NO 30
<211> LENGTH: 12
<212> TYPE: PRT
<213> ORGANISM: artificial sequence
<220> FEATURE:
<223> OTHER INFORMATION: peptide specific to Langerhans dendritic cells
<220> FEATURE:
<221> NAME/KEY: MISC_FEATURE
<222> LOCATION: 10
<223> OTHER INFORMATION: Xaa is any amino acid

<400> SEQUENCE: 30

Lys Ile Met Gln Ser Pro Leu Gln His Xaa Ala Pro
                5                   10
```

```
<210> SEQ ID NO 31
<211> LENGTH: 12
<212> TYPE: PRT
<213> ORGANISM: artificial sequence
<220> FEATURE:
<223> OTHER INFORMATION: peptide specific to Langerhans dendritic cells
<220> FEATURE:
<221> NAME/KEY: MISC_FEATURE
<222> LOCATION: 4
<223> OTHER INFORMATION: Xaa is any amino acid

<400> SEQUENCE: 31

Lys Val Trp Xaa Ile Asp Trp Pro Pro Pro Ala Tyr
                5                   10

<210> SEQ ID NO 32
<211> LENGTH: 12
<212> TYPE: PRT
<213> ORGANISM: artificial sequence
<220> FEATURE:
<223> OTHER INFORMATION: peptide specific to Langerhans dendritic cells
<220> FEATURE:
<221> NAME/KEY: MISC_FEATURE
<222> LOCATION: 10
<223> OTHER INFORMATION: Xaa is any amino acid

<400> SEQUENCE: 32

Ala Asp Arg Ser Arg Glu Leu Ala Leu Xaa Ile Phe
                5                   10

<210> SEQ ID NO 33
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 33

Ile Ile Pro Ser Thr Ala Asn Lys Ser Ile Ala Thr
                5                   10

<210> SEQ ID NO 34
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 34

Ser Asn Leu Ser Arg Thr Thr Leu Tyr Ser Gln Val
                5                   10

<210> SEQ ID NO 35
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 35

His Ser Leu Arg Ser Asp Trp Val Ser Pro Asn Thr
                5                   10

<210> SEQ ID NO 36
<211> LENGTH: 12
```

```
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 36

Ser Ser Thr Ile Asn Tyr Asn Arg Leu Asn Leu His
                5                   10

<210> SEQ ID NO 37
<211> LENGTH: 12
<212> TYPE: PRT
<213> ORGANISM: artificial sequence
<220> FEATURE:
<221> NAME/KEY: PEPTIDE
<223> OTHER INFORMATION: peptide specific to Langerhans dendritic cells

<400> SEQUENCE: 37

Ser Leu His Arg Ser Ser Ser Leu Pro Ile Ser Thr
                5                   10

<210> SEQ ID NO 38
<211> LENGTH: 12
<212> TYPE: PRT
<213> ORGANISM: artificial sequence
<220> FEATURE:
<221> NAME/KEY: PEPTIDE
<223> OTHER INFORMATION: peptide used as negative control

<400> SEQUENCE: 38

Glu Pro Ile His Pro Glu Thr Thr Phe Thr Asn Asn
                5                   10

<210> SEQ ID NO 39
<211> LENGTH: 95
<212> TYPE: DNA
<213> ORGANISM: artificial sequence
<220> FEATURE:
<223> OTHER INFORMATION: forward primer to fusion protein of DC-
      binding peptide 3 and immunodominant domains
      of HER2/Neu

<400> SEQUENCE: 39
catgccatgg agaagatctt tgggagcctg gcatttctgc cggagagctt          50
tgatggggac cctcgaggcg gaggtcgtag actgctgcag gaaac              95

<210> SEQ ID NO 40
<211> LENGTH: 80
<212> TYPE: DNA
<213> ORGANISM: artificial sequence
<220> FEATURE:
<223> OTHER INFORMATION: reverse primer to fusion protein of DC-
      binding peptide 3 and immunodominant
      domains of HER2/Neu

<400> SEQUENCE: 40
gccggtacct gggggtccct ggccatgcgg gagaattcag acaccaactc          50
tccgccaccg ctaggtgtca gcggctccac                               80
```

DENDRITIC CELL BINDING PROTEINS AND USES THEREOF

CROSS-REFERENCE TO RELATED APPLICATIONS

This international application claims benefit of provisional U.S. Ser. No. 60/461,474, filed Apr. 9, 2003.

BACKGROUND OF THE INVENTION

1. Field of the Invention

The present invention relates generally to the field of immunology. More specifically, it relates to dendritic cell binding proteins and uses thereof.

2. Description of the Related Art

Dendritic cells (DCs) are a complex, heterogeneous group of multifunctional antigen presenting cells. Dendritic cells comprise an essential component of the immune system. The role of these cells has been repeatedly highlighted in cancer and infectious diseases. Recently, there have been great insights into the origins of dendritic cell subsets and their modulation by distinct cytokines of neighboring cells.

Dendritic cells differentiate into at least three pathways: myeloid (MDC), plasmacytoid (LDC), and Langerhans cell (LC) (1-7). Progenitors of myeloid dendritic cells in bone marrow migrate via the blood stream and home to the peripheral tissues ready to confront invading pathogens. In such environments, dendritic cells ingest antigens via several mechanisms including phagocytosis and receptor-mediated endocytosis. Langerhans cells phagocytose, process, and present protein antigens to T cells. Antigenic infectious agents including vaccines induce pro-inflammatory cytokines, e.g., TNF-a. These cytokines promote Langerhans cell maturation and migration to plasmacytoid organs where they home to the T cell rich area.

Langerhans cells undergo phenotypic and functional changes during their maturation and migration. These cells, which are now loaded with antigenic peptides on MHC class II, down-regulate CD1a, CCR6, and E-cadherin, and lose the capacity to capture foreign antigens. Human $CD14^+$ progenitor dendritic cells cultured in GM-CSF+IL-4 are equivalent to interstitial dendritic cells, i.e., dermal dendritic cells, and express CD1a, CD64 and Factor IIIa. By contrast, monocytes cultured with M-CSF convert to a macrophage phenotype. These myeloid dendritic cells may home within plasmacytoid follicles, where they reside as germinal center dendritic cells. In this area, germinal center dendritic cells establish the contact between T- and B-cells, which may lead to the stimulation of an active immune response.

Dendritic cells present processed antigenic peptides on MHC class II molecules to $CD4^+$ T cells, which will be activated in conjunction with co-stimulatory signals such as CD40 and CD86 delivered from dendritic cells in plasmacytoid organs. Several receptors and their ligands are involved in the T cell/dendritic cell dialogue, such as CD40/CD40L. For instance, up-regulation of CD40L on T cells facilitates dendritic cell maturation. Activated dendritic cells then release cytokines such as IL-12, which modulate and stimulate the production of interferon (IFN)-γ from T cells. In situ, activated dendritic cells can prime naïve $CD8^+$ T cells, or they undergo apoptosis. Activated T cells, via activated adhesion molecules, migrate to the area of the B-cell follicles. There they interact with naïve antigen-specific B cells. T- and B-cell interaction results in the clonal expansion of B cells, which takes place in the plasma foci of the T cell rich area and in the germinal centers. T- and B-cell dialogue in the germinal center might be influenced by germinal center dendritic cells and follicular dendritic cells.

Peyer's patch dendritic cells are critical components of mucosal-associated plasmacytoid tissue (MALT). The Peyer's patch is the primary mucosal site for antigen processing in the intestine. Recent in vivo studies provide evidence that dendritic cell network in the subepithelial dome of Peyer's patch is a critical component in the uptake and processing of luminal antigens. Such uptake may occur by endocytosis or by phagocytosis after passage of antigen through M cells. The dendritic cells then present the processed antigen to $CD4^+$ or $CD8^+$ T cells in the subepithelial dome, or after maturation and migration, to the interfollicular regions where antigen is presented to $CD4^+$ or $CD8^+$ T cells. In this regard, immunohistologic analysis of dendritic cell subsets including LCs in Peyer's patch has revealed that the unique microanatomical localization of dendritic cell subsets enables them to regulate specific T- and B-cell responses in vivo.

To date, most studies of dendritic cells in oral mucosa have focused on immature dendritic cells (Langerhans cells). Immature dendritic cell subsets have been observed to increase in number in oral mucosa affected by gingivitis-periodontitis, oral lichen planus, histocytosis X, oral candidiasis, and contact hypersensitivity responses to dental material and oral cancer. Most often, the distribution of dendritic cells in oral mucosa parallels that of T cells, suggesting that these dendritic cells are engaged in antigen presentation in situ.

The human immunodeficiency virus (HIV) epidemic has killed more than 24 million people and more than 40 million individuals are infected with HIV as cited in UNAIDS, 2001. Mucosal cells that cover all the cavities of the body including mouth are portals of HIV entry. Specific protective effector cells are incompletely characterized, but it is likely that immunity to chronic infection is mediated primarily by cellular defenses, including HIV-specific CTLs. A safe and effective vaccine for HIV that can be prepared easily in large quantities and delivered on a global scale is needed urgently to halt this epidemic.

The hypermutability of the HIV genome is a major challenge for vaccine development. Purified subunit vaccines rely heavily on the antibody response for protection, and this has been recognized for some time to be a severe limitation for vaccines against viruses, especially MV. Thus, several research groups have attempted to prepare vaccines that induce specific cellular immune responses. This strategy deals with viral gene products that are not exposed to antibody and thus exhibit less variability than the envelope glycoprotein. For HIV, novel recombinant viruses and pure DNA vaccines induce weak antibody responses. Thus, promising vaccine protocols entail priming with DNA or virus and a boosting with purified envelope glycoprotein.

Hepatitis C virus (HCV), a member of the Flaviviridae, is a positive-sense, single-stranded RNA with genome size of 9.4 kb, identified in 1989 as the major etiologic agent of non-A, non-B hepatitis. Hepatitis C virus infects not only hepatocytes, but may also infect lymphocytes and monocytes. A disturbing feature of hepatitis C virus is its long-term persistence in the host, followed by chronic liver disease and the associated possibilities of hepatocellular carcinoma, cryoglobulinemia, and autoimmunity. The current therapy for hepatitis C virus is type I interferon plus ribavirin in combination. However, less than 41% of patients respond.

DC as a critical vector for vaccine strategy induce potent antigen-specific immunity in various settings including human clinical trials (8-10). Optimal means of delivering immunogenic antigen to DC remain undefined, but current immunotherapy relies largely on ex vivo methods. While useful to demonstrate proof-of-concept, ex vivo growth of DC is logistically difficult (24). While DC based immunotherapy highlighted its critical role in inducing antigen specific immunity, however at present, DC-targeting strategies are hampered by lack of DC-specific target molecules.

The prior art is deficient in the lack of novel dendritic cell binding peptides and uses thereof. The present invention fulfills this long-standing need and desire in the art.

SUMMARY OF THE INVENTION

The present invention is directed to novel peptides which specifically targets and binds to dendritic cells.

The present invention also is directed to a fusion protein comprising a peptide that specifically targets and binds to dendritic cells and a non-dendritic cell protein.

The present invention is directed further to a DNA encoding a peptide which specifically targets and binds to dendritic cells or encoding a fusion protein comprising the peptide and a non-dendritic cell protein.

The present invention is directed further to a vaccine delivery system. The system comprises a peptide that specifically targets and binds to dendritic cells and a pathogen-specific protein or tumor specific antigen.

The present invention is directed further still to a method of promoting an immune response in an individual in need of such treatment. The method comprises administering to the individual an effective amount of a composition comprising a peptide which specifically targets and binds to dendritic cells and a pathogen or antigen specific protein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

In FIG. 1A MDC were stained with biotinylated DC-peptides # 3, 12, 18, control peptide, CD1a, HLA-DR and CD11c and analyzed by FACS. In FIG. 1B DC were stained with biotinylated DC-peptides or control peptide, fixed, permeabilized, conjugated with Streptavidin (SA)-Alexa 488 and visualized by confocal microscopy (40×). Monocytes (FIG. 1C), or T and B cells (FIG. 1D) were stained with biotinylated DC-peptides, or control peptide, conjugated with SA-PE and analyzed by FACS. In FIG. 1E Rhesus macaques monocytes-derived DC were stained with biotinylated DC-peptides or control peptides and analyzed by FACS. In FIG. 1F FACS analysis of bone marrow derived DC stained with biotinylated DC-peptides or control conjugated with SA-PE. All experiments were repeated at least three times.

In FIG. 2A DC were stained with biotinylated DC-peptides (thick lines), or control peptide (thin lines), or after pretreatment with the same peptide not biotinylated (dotted line), and were analyzed by FACS. In FIG. 2B incubation with a given DC-binding peptide did not inhibit binding of other DC-binding peptides. DC were first treated with unlabeled peptides (biotin free), stained with biotinylated peptides, conjugated with SA-PE, and analyzed by FACS. In FIG. 2C DC were incubated with various concentrations of DC-binding peptides or control peptide, conjugated with SA-PE, fixed and analyzed by FACS. The X-axis depicts mean fluorescence intensity (MFI) of gated events. In FIG. 2D MDC were treated with biotinylated DC-peptides for 0, 2, 4, or 20 hrs and analyzed by FACS. Data represent the mean of three experiments. In FIG. 2E DC were activated with E. coli LPS (100 ng/ml) for 48 hrs and stained with biotinylated DC-peptides or control peptide, and analyzed by FACS. All experiments were performed at least three times.

FIG. 3A-3C demonstrate that DC-binding peptides did not change the phenotype or functions of DC. In FIG. 3A The phenotype of DC treated with DC-peptides was analyzed by FACS. Untreated DC (thick line); DC treated with peptides (dotted line); and isotype control (dashed line). DC treated simultaneously with DC-peptides did not inhibit the proliferation of allogeneic CD4$^+$ T cells (FIG. 3B) or T cell activation (FIG. 3C). All experiments were repeated at least three times.

In FIG. 4A a schematic depicting of the NS3-FP or NS3-control FP construct. In FIG. 4B the SDS-PAGE of the Ni$^{++}$-affinity-purified products (left panel) and Western blot (right panel). The transferred proteins were detected using an anti-NS3 antibody and visualized by ECL western blotting detection system. In FIG. 4C detection of NS3-FP using a monoclonal anti-NS3 antibody conjugated with a goat anti-mouse IgG FITC by FACS analysis; NS3-FP (thick line), NS3-cFP (dotted line), or isotype control (thin line).

In FIGS. 5A-5D DCs were incubated with NS3-FP (1 µg/ml), NS3-cFP (1 µg/ml), NS3 alone (1 µg/ml) alone, or nothing for 12 hrs at 37° C. Pulsed and impulsed DCs were cocultured at graded doses with autologous CD4$^+$ (FIG. 5A) or CD8$^+$ T cells (FIG. 5B) derived from HCV$^+$ PBMCs for 4 days at 37° C. T cell proliferation was assayed by [$^3$H] thymidine incorporation (mean of triplicate wells±SD is shown). Supernatants of these cocultures were assayed for CD4$^+$ (FIG. 5C) and CD8$^+$ T cell cytokines (FIG. 5D) by ELISA. In FIG. 5E aliquots of DC pulsed with NS3-FP, NS3-cFP (lower panels, thick line) or nothing (thin line) were analyzed by FACS. In FIG. 5F the supernatants of pulsed DC with NS3-FP, NS3-cFP, or nothing were analyzed for IL-12 p70 production by ELISA. All experiments were repeated at least three times.

In FIG. 6A An aliquot of enriched T cells of recovered PBMCs from the peritoneum of each mouse-group were stained with CD3/CD4/CD8/CD69 and analyzed FACS. In FIG. 6B Intracellular cytokine production was assessed as described by gating on CD3$^+$ cells. In FIG. 6C induction of autologous CD4$^+$ T cell proliferation by DC pulsed with NS3, HIV gp160 (irrelevant antigen), or nothing. 6D: Cytokines of CD4$^+$ T cells were assayed by ELISA. In FIG. 6D DCs pulsed with NS3 or HIV-gp160 were activated with proinflammatory cytokines and subsequently cocultured with purified CD8$^+$ T cells from each immunized mouse group for 4 days. [$^3$H] thymidine incorporation was measured 16 hrs later (mean of triplicate wells±SD is shown). In FIG. 6F analysis of cytokines released by CD8$^+$ T cells by ELISA. All experiments were repeated three times.

10³/Mouse), NS3-FP (1 μg/mouse), NS3-cFP (1 μg/ml) or no supplement by footpad injection. After the fourth immunization spleens and lymph nodes were derived from immunized mice and cell suspensions were prepared. T cell proliferation by [³H] thymidine incorporation and T cell activation by cytokine analysis were determined.

Figure 8A:
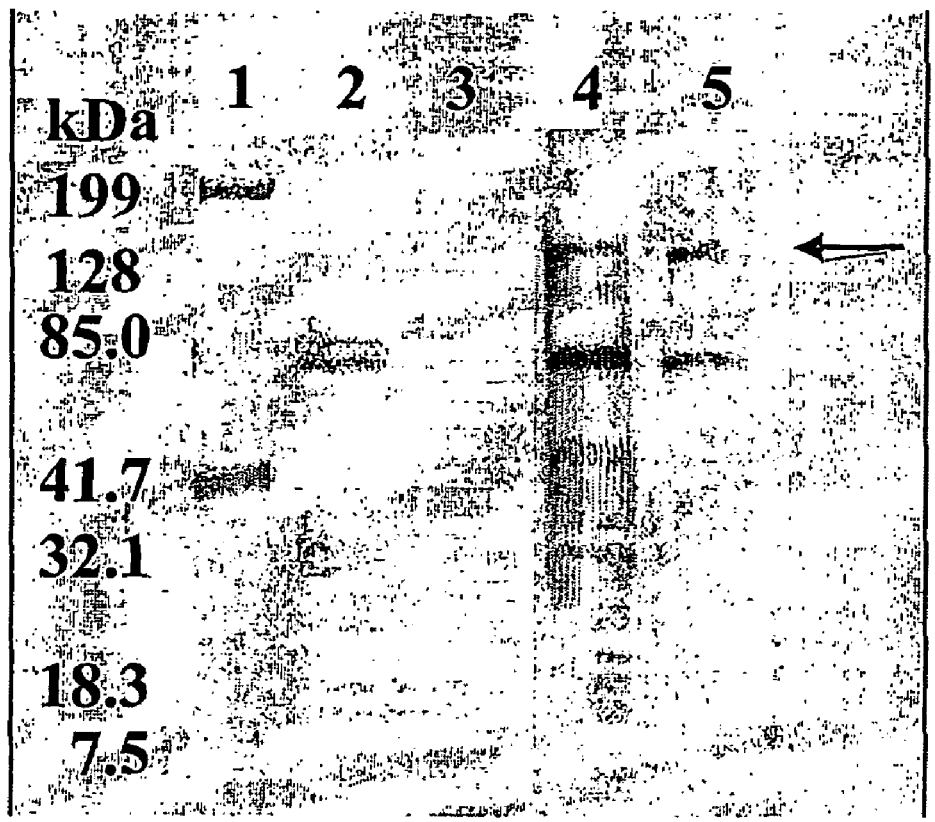
Figure 8B:
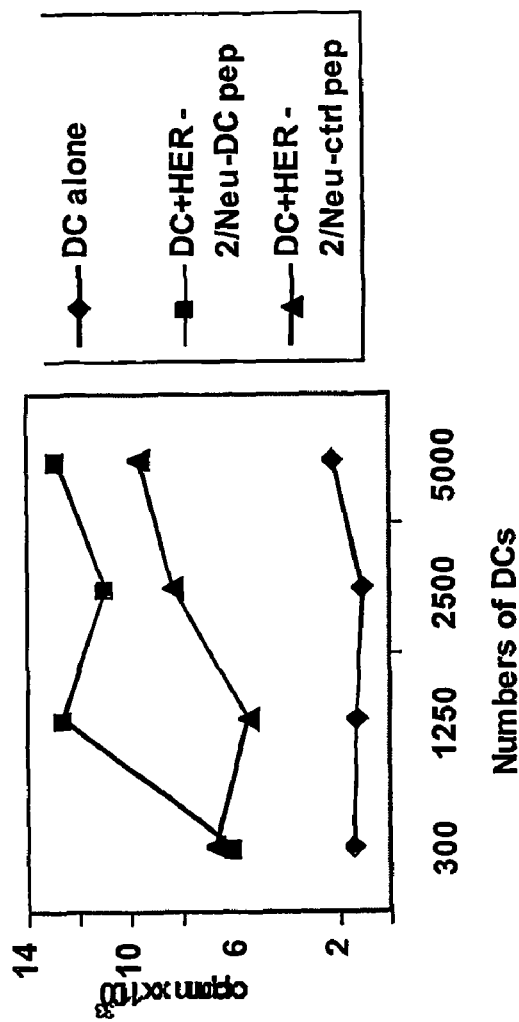
Figure 8C:
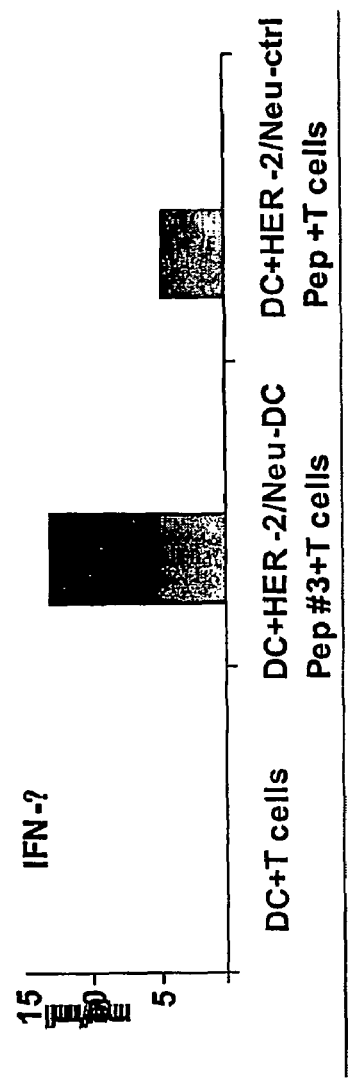

FIGS. 8A-8C demonstrate fusion of DC-peptide with HER-2/Neu. In FIG. 8A the nickel-affinity-purified full-length fusion protein and three major bands. Lane 1, ladder; Coomassie blue staining of purified HER-2/Neu-control peptide (lane 2) and purified HER-2/Neu-DC peptide# 3 (lane 3), ECL detection of purified HER-2/Neu-control peptide (lane 4), and purified HER-2/Neu-DC-peptide # 3 (lane 5). In FIG. 8B DCs were pulsed with HER-2/Neu-DC peptide# 3, HER-2/Neu-ctrl peptide fusions or nothing for 12 hrs at 37° C. DCs were then cocultured with human autologous CD4 and CD8⁺ T cells for 4 days. Sixteen hrs later, [³H] thymidine was added and T cell proliferation was measured by a β-counter. In FIG. 8C: Cytokines of activated T cells by pulsed DCs were analyzed by ELISA.

Figure 9B:
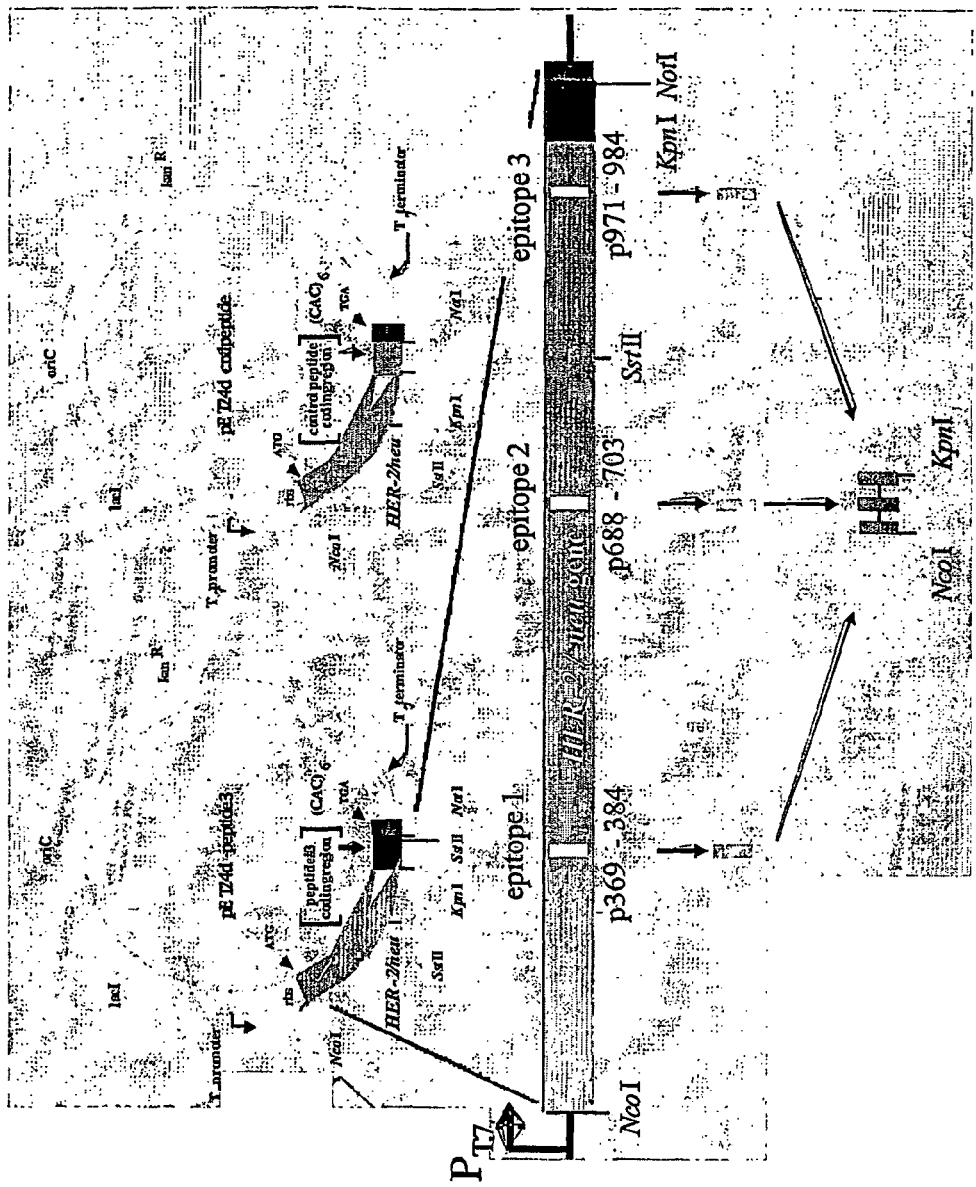

FIGS. 9A-9B shows fusion of DC-binding peptide #3 with the immunodominant domains of HER2/Neu. FIG. 9A depicts the forward primer (SEQ ID NO: 39) and the reverse primer (SEQ ID NO: 40). The bold regions are restriction sites, the underlined regions are the HER2/Neu epitopes and the double underlined region anneals to the DNA encoding epitope 2. FIG. 9B is a schematic depicting the construct.

DETAILED DESCRIPTION OF THE INVENTION

One embodiment of the present invention provides a novel peptide that specifically targets and binds to dendritic cells. In one aspect, the dendritic cell is a myeloid dendritic cell. For example, the myeloid dendritic cell peptide may be a 12 amino acid residue peptide. Representative examples of such 12 amino acid residue peptide include MDC peptides having sequences shown in SEQ ID NOS: 1-20.

In another aspect, the dendritic cell is a Langerhans cell. For example, the Langerhans cell peptide also may be a 12 amino acid residue peptide. Representative examples of such 12 amino acid residue peptide include LC peptides having sequences shown in SEQ ID NOS: 21-37. In a further aspect, the dendritic cell is a plasmacytoid dendritic cell.

In a related embodiment the present invention provides a peptide which specifically targets and binds to dendritic cells having a sequence at least 80% homology to a peptide having an amino acid sequence selected from the group consisting of SEQ ID NOS: 1-20. Alternatively, the amino acid sequence is selected from the group consisting of SEQ ID NOS: 21-37.

In another embodiment of the present invention there is provided a fusion protein, comprising a peptide which specifically targets and binds to dendritic cells; and a non-dendritic cell protein or fragments thereof. In this embodiment the non-dendritic cell protein may be a tumor associated antigen. The tumor associated antigen may be Melan A, MAG-3, gp100, or HER2/Neu. The non-dendritic cell protein may be an inhibitor of dendritic cell function or activity.

In a related embodiment there is provided a peptide which specifically targets and binds to dendritic cells having a sequence at least 80% homology to a peptide having an amino acid sequence selected from the group consisting of SEQ ID NOS: 1-20; and a non-dendritic cell protein or a fragment thereof. The non-dendritic cell protein may be a tumor associated antigen. Examples of an antigen are Melan A, MAG-3, gp100 or HER2/Neu.

Alternatively, the peptide may have a sequence with at least 80% homology to a peptide having an amino acid sequence selected from the group consisting of SEQ ID NOS: 21-37. In this alternative embodiment the tumor associated antigen may be Melan A, MAG-3, gp100, or HER2/Neu. In either embodiment the non-dendritic cell protein may be an inhibitor of dendritic cell function or activity.

In yet another embodiment of the present invention there is provided a DNA sequence encoding a peptide which specifically targets and binds to dendritic cells. In one aspect of this embodiment the DNA sequence encodes a peptide having at least 80% homology to a peptide having an amino acid sequence selected from the group consisting of SEQ ID NOS: 1-20. Alternatively, the DNA encodes a peptide having at least 80% homology to a peptide having an amino acid sequence selected from the group consisting of SEQ ID NOS: 21-37. In all aspects of this embodiment the dendritic cells are as described supra.

In a related embodiment there is provided a DNA sequence encoding a fusion protein where the fusion protein comprises a peptide which specifically targets and binds to a dendritic cell; and a non-dendritic protein or a fragment thereof. In all aspects of this embodiment the peptide may be and have those amino acid sequences described supra. Additionally, the non-dendritic cell protein and the functions thereof are as described supra.

In still another embodiment of the present invention there is provided a vaccine delivery system comprising a peptide which specifically targets and binds to dendritic cells; and a virus specific protein or a bacteria specific protein or a tumor associated antigen or fragments thereof. In this embodiment the virus specific protein may be from viruses such as HCV, HIV, Ebola, rotavirus, or any pathogenic human virus. In one aspect the HCV protein is NS3, E1 or E2. In another aspect the HIV protein is Nef, gp120 or gag. In a further aspect the Ebola protein is subunit GP or subunit VP40.

Also in this embodiment, the bacteria specific protein may be from *Bacillus anthracis* or *Yersinia pestis* or any pathogenic human bacterium. The *B. anthracis* protein is protective antigen. The *Y. pestis* protein may be F1-V. Further in this embodiment the tumor associated antigen may be Melan A, MAG-3, gp100, or HER2/Neu.

In all aspects of this embodiment the peptide, the virus specific protein, the bacteria specific protein and the tumor associated antigen may be expressed in a bacterial host. An example of a bacterial host is *Salmonella*. Additionally, in all aspects the dendritic cells may be as described supra. Furthermore, in all aspects the peptide may be and have those amino acid sequences described supra.

In a related embodiment there is provides a multivalent delivery system comprising at least two peptides which specifically target and bind to dendritic cells; and at least two virus specific proteins.

In still another embodiment of this invention there is provided a method promoting an immune response in an individual in need of such treatment, comprising administering to the individual an effective amount of a composition which comprises a peptide which specifically targets and binds to dendritic cells; and a virus specific protein, a bacteria specific protein. In this embodiment the dendritic cells are as described supra. Also, the peptide may be and have those amino acid sequences described supra. Furthermore, the virus specific proteins, the bacteria specific proteins and the tumor associated antigens may be as described supra and the peptide and the virus or bacterial specific proteins or the tumor associated antigen may be expressed in a bacterial host as described.

The practice of the present invention will employ, unless otherwise indicated, conventional techniques of immunology, molecular biology, microbiology, cell biology and recombinant DNA, which are within the skill of the art, are found in Sambrook, et al., Molecular Cloning: A Laboratory Manual (2nd Ed., Vols. 1-3, Cold Spring Harbor Laboratory (1989)), Methods in Enzymology, Vol. 152: Guide to Molecular Cloning Techniques (Berger and Kimmel (eds.), San Diego. Academic Press, Inc. (1987)), or PCR 2: A Practical Approach (MacPherson, et al. (eds.)) Academic Press, Inc. (1995) or Current Protocols in Molecular Biology, (Ausubel, et al. (eds.), Greene Publishing and Wiley-Interscience, New York (1987) or Antibodies, A Laboratory Manual, And Animal Cell Culture (R. I. Freshney, ed. (1987)) or later editions thereof.

As used herein, certain terms may have the following defined meanings.

As used in the specification and claims, the singular form "a", "an" and "the" include plural references unless the context clearly dictates otherwise. For example, the term "a cell" includes a plurality of cells, including mixtures thereof.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, rib ozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules. "Oligonucleotide" refers to polynucleotides of between about 5 and about 100 nucleotides of single- or double-stranded DNA. Oligonucleotides are also known as oligomers or oligos and may be isolated from genes, or chemically synthesized by methods known in the art.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (see Sambrook et al., supra). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

A "gene delivery vehicle" is defined as any molecule that can carry inserted polynucleotides into a host cell. Examples of gene delivery vehicles are liposomes, viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well-characterized, homogenous group of viruses, including over 50 serotypes as in, e.g., WO 95/27071. Ads are easy to grow and do not require integration into the host cell genome. Recombinant Ad-derived vectors, particularly those that reduce the potential for recombination and generation of wild-type virus, have also been constructed as disclosed in, for example, WO 95/00655 and WO 95/11984. Wild-type AAV has high infectivity and specificity integrating into the host cells genome. See for example Hermonat and Muzyczka (1984) PNAS USA 81:6466-6470 and Lebkowski, et al. (1988) Mol. Cell. Biol. 8:3988-3996).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., TCR, CD3 or CD4.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1.sub.I), interleukin-11 (IL-11), MIP-1α, leukemia inhibitory factor (LIF), c-kit ligand, thrombopoietin (TPO) and flt3 ligand. The present invention also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), and R&D Systems (Minneapolis, Minn.). It is intended, although not always explicitly stated, that molecules having similar biological activity as recombinant or purified cytokines (recombinantly produced or mutants thereof) are intended to be used within the spirit and scope of the invention.

"Co-stimulatory molecules" are involved in the interaction between receptor-ligand pairs expressed on the surface of antigen presenting cells and T cells. One exemplary receptor-ligand pair is the B7 co-stimulatory molecules on the surface of dendritic cells and its counter-receptor CD28 or CTLA-4 on T cells (18-20). Other important co-stimulatory molecules include CD40, CD54, CD80, CD86, B7-H1 and B7-H2 (ICOS ligand). See, for example, Freeman, et al. (1993) Science 262:909-91 1; Young, et al. (1992) J. Clin. Invest. 90: 229; Nabavi, et al. (1992) Nature 360:266

The terms "antigen-presenting cells" or "APCs" includes both intact, whole cells as well as other molecules which are capable of inducing the presentation of one or more antigens, preferably in association with class I or class II MHC molecules. Examples of suitable antigen-presenting Cells are discussed in detail below and include, but are not limited to, whole cells such as macrophages, dendritic cells, B cells, purified MHC class I or class II molecules; and foster antigen presenting cells.

Dendritic cells (DCs) are potent antigen-presenting cells. It has been shown that dendritic cells provide all the signals required for T cell priming, activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. This interaction is necessary, but not sufficient, for T cell activation to occur. In fact, without the second type of signals, the first type of signals can result in T cell anergy. The second type of signals, called co-stimulatory signals, is neither antigen-specific nor MHC-restricted, and can lead to a full proliferation response of T cells and induction of T cell effector functions in the presence of the first type of signals. As used herein, "dendritic cell" is to include, but not be limited to a pulsed dendritic cell, a foster cell or a dendritic cell hybrid.

The term "immune effector cells" refers to cells capable of binding an antigen or which mediate an immune response. These cells include, but are not limited to, T cells, B cells, monocytes, macrophages, NK cells and cytotoxic T lymphocytes (CTLs). Certain diseased tissue expresses specific antigens and CTLs specific for these antigens have been identified. For example, approximately 80% of melanomas express the antigen known as gp 100.

A "naive" cell is a cell that has never been exposed to the antigen recognized by its antigen receptor.

The term "culturing" refers to the in vitro propagation of cells or organisms on or in media of various kinds. It is understood that the descendants of a cell grown in culture may not be completely identical, e.g., morphologically, genetically, or phenotypically, to the parent cell. By "expanded" is meant any proliferation or division of cells.

A "subject" is a vertebrate, preferably a mammal, more preferably a human. Mammals include, but are not limited to, murines, simians, humans, farm animals, sport animals, and pets.

The terms "major histocompatibility complex" or "MHC" refers to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified class I, class II MHC molecules and non-classical MHC. Class I AMC molecules include membrane heterodimeric proteins made up of an alpha. chain encoded in the MHC associated noncovalently with beta.-microglobulin. Class I MHC molecules are expressed by nearly all nucleated cells and have been shown to function in antigen presentation to CD8+ T cells. Class I molecules include HLA-A, -B, and -C in humans. Class II MHC molecules also include membrane heterodimeric proteins consisting of noncovalently associated alpha. and beta. chains. Class II MHC are known to participate in antigen presentation to CD4+ T cells and, in humans, include HLA-DP, -DQ, and DR. The term "MHC restriction" refers to a characteristic of T cells that permits them to recognize antigen only after it is processed and the resulting antigenic peptides are displayed in association with either a self class I or class II MHC molecule. Methods of identifying and comparing MHC are well known in the art and are described in Allen, M. et al. (1994) *Human Imm.* 40:25-32; Santamaria, P. et al. (1993) *Human Imm.* 37:39-50 and Hurley, C. K. et al. (1997) *Tissue Antigens* 50:401-415.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

A "control" is an alternative subject or sample used in an experiment for comparison purpose. A control can be "positive" or "negative". For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

"PCR primers" refer to primers used in "polymerase chain reaction" or "PCR," a method for amplifying a DNA base sequence using a heat-stable polymerase such as Taq polymerase, and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce exponential and highly specific amplification of the desired sequence (see PCR 2: A Practical Approach, supra). PCR also can be used to detect the existence of the defined sequence in a DNA sample.

"Host cell" or "recipient cell" is intended to include any individual cell or cell culture that can be or have been recipients for vectors or the incorporation of exogenous nucleic acid molecules, polynucleotides and/or proteins. It also is intended to include progeny of a single cell, and the progeny may not necessarily be completely identical, e.g., in morphology or in genomic or total DNA complement, to the original parent cell due to natural, accidental, or deliberate mutation. The cells may be prokaryotic or eukaryotic, and include but are not limited to bacterial cells, yeast cells, animal cells, and mammalian cells, such as from mice, rats, primates or humans.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody, as defined above, and its binding partner or ligand. A native antigen is a polypeptide, protein or a fragment containing an epitope, which induces an immune response in the subject.

The term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

An "isolated" or "enriched" population of cells is "substantially free" of cells and materials with which it is associated in nature. By "substantially free" or "substantially pure" means at least 50% of the population are the desired cell type, preferably at least 70%, more preferably at least 80%, and even more preferably at least 90%.

A "composition" is intended to mean a combination of active agent and another compound or composition, inert, for example, a detectable agent, solid support or label, or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. Examples of carriers, stabilizers and adjuvants are well known in the art and described in Remington's Pharmaceutical Sciences, 15th edition, Mack Publishing Co., (Easton, Pa., 1985) and later editions.

An "effective amount" is an amount sufficient to effect beneficial or desired results. An effective amount can be administered in one or more administrations, applications or dosages.

Provided herein are novel peptides that specifically target and bind to dendritic cells and vaccines and methods of use. The peptides comprise about twelve amino acid residues and are specific for myeloid dendritic cells (MDC), Langerhans dendritic cells (LC) and plasmacytoid dendritic cells (LDC). Representative sequences for MDCs and LCs are shown in Table 1. The peptides described herein further may comprise a means to specifically target and bind to dendritic cells in larger, mixed cell populations for their identification and purification.

It is well established in this art that a person having ordinary skill would be readily able to manipulate these 12 amino acid residue peptides by substituting one amino acid for another without affecting adversely the ability of the peptide to specifically target and bind to dendritic cells. For example, a useful peptide may have 80% homology to the novel peptides presented herein.

TABLE 1

| SEQ ID | MDC-Peptides | SEQ ID | LC Peptides |
|---|---|---|---|
| 1 | YPIVNTAVATHM | 21 | SITQHLQLKPLA |
| 2 | ATFTVGPPQLLR | 22 | VSHPLWHPXRIL |
| 3 | FYPSYHSTPQRP | 23 | VSSPPRVSGIGL |
| 4 | TSIGTHXLSAAL | 24 | HPPEIYSPPRYP |
| 5 | TETSWSMFPLHL | 25 | HSLRLDFMAPLT |
| 6 | APHLPYLRGLNL | 26 | LPPGADLYFHPS |
| 7 | HHNSNERSFHYL | 27 | IPPLRITEVTPT |

TABLE 1-continued

| SEQ ID | MDC-Peptides | SEQ ID | LC Peptides |
|---|---|---|---|
| 8 | SYANLIRSIQPG | 28 | IRHTTSGPPPSS |
| 9 | TLVHQWQPWPKA | 29 | VSSPPRVSGIGL |
| 10 | IRHTTSGPPPSS | 30 | KIMQSPLQHXAP |
| 11 | YPQALNTQPDWP | 31 | KVWXIDWPPPAY |
| 12 | AYYKTASLAPAE | 32 | ADRSRELALXIF |
| 13 | SQNSLYSSKPVR | 33 | IIPSTANKSIAT |
| 14 | SLSLLTMPGNAS | 34 | SNLSRTTLYSQV |
| 15 | QSQTYQTHSVTM | 35 | HSLRSDWVSPNT |
| 16 | EPIHPETTFTNN | 36 | SSTINYNRLNLH |
| 17 | ETPMVHWPSTSP | 37 | SLHRSSSLPIST |
| 18 | SLSLLTMPGNAS | | |
| 19 | NWWSDWVMLTQS | | |
| 20 | QWPQYHYLRPTL | | |

The peptides may comprise a composition designed to target and to deliver the peptide. For example a fusion protein comprising a peptide and non-dendritic cell protein may be utilized. More specifically, the fusion protein may comprise the peptide and a tumor associated antigen (TAA), such as to a solid tumor. Alternatively, the immunodominant domains of the TAAs may be used fused to the peptides described herein. Hundreds of representative tumor associated antigens are well known in the art. They may be, although not limited to Melan A, MAG-3, gp100 or her2/neu.

Alternatively, the non-dendritic cell protein may an inhibitor of dendritic cell function or activity. For example p38 mitogen activated protein kinase inhibitors may comprise the fusion protein with the peptide. Alternatively, a compound with inhibitory properties may be used. Representative examples of useful inhibitors include 1,4-diamino-2,3-dicyano-1,4-bis(2-aminophenylthio)butadiene, 4-(4-fluorophenyl)-2-(4-methylsulfinyl phenyl)-5-(4-pyridyl)H-limidazole, anthral[1,9-cd]pyrazol-6(2H)-one 1,9-pyrazoloanthrone and sp600125. It is contemplated further that immunotherapeutics such as interferons or chemotherapeutics such as anthracyclines may be conjugated to the fusion protein.

Furthermore, the dendritic cell binding peptides of the present invention can facilitate the internalization of any immune gene of interest. As described above, these dendritic cell binding peptides can be conjugated to inhibitors of interest. Conjugated peptides with inhibitors can be up taken by dendritic cells and such inhibitors can inhibit the function(s) of dendritic cells such as, but not limited to antigen processing presentation functions of dendritic cells.

Alternatively, the composition may comprise the peptides and a virus or pathogen specific protein or a tumor associated antigen or transplant antigen or fragments of any suitable antigen to be used as a vaccine delivery system. A virus antigen or other suitable antigen may be from, but not limited to, HCV, HIV, rotavirus, or Ebola virus. HCV proteins may include NS3, NS4A, E1, and E2. HIV proteins may include Nef, gp120, gag and envelope proteins: A representative Ebola virus protein is subunit GP or subunit VP40. As described above, a tumor associated antigen may be Melan A, MAG-3, gp100 or HER2/Neu. Furthermore, in the vaccine delivery system of the present invention, the peptide and said protein may be expressed in a bacterium or other host as is well known in the art.

Additionally, it is contemplated that a recombinant adenoviral vector may comprising DNA encoding a peptide which specifically targets and binds to dendritic cells. This recombinant adenoviral vector may further DNA encoding a fusion protein comprising the peptide and a non-dendritic cell protein, such as a tumor associated antigen. Alternatively the vector may comprise DNA encoding an inhibitor of dendritic cell function or activity as presented herein. One of skill in the art will appreciate that the techniques to construct such recombinant adenoviral vectors are well known in the art.

As such the present invention further provides a DNA encoding a peptide that specifically targets and binds to a dendritic cell. Alternatively, the DNA may encode a peptide having 80% homology to the novel peptides provided herein. Furthermore, the DNA may encode a fusion protein comprising these peptides and a non-dendritic cell protein as presented herein. Techniques useful for the practice of this aspect of the invention are well-known and standard in the art and are described supra.

The peptides, fusion compositions and vaccine delivery systems are useful to promote an immune response in an individual such as a human or nonhuman mammal. An immunogenic composition comprising one or more peptides and one or more virus specific proteins or a tumor associated antigen as described herein is administered in an effective amount to elicit an immune response. It is contemplated that the immunogenic composition is taken up, internalized, processed by dendritic cells and presented to T cells. Furthermore, the interaction between the DC-peptides and their cognate surface ligands may prevent signals leading to tolerance. Moreover, DC-targeted fusion proteins captured by DC do not appear to impair accessory immunological responses.

Such a strategy may mediate therapeutic immunity and mobilize strong immune responses against pathogenic viruses, such as, but not limited to, HIV, SIV, Ebola or against tumor cells, such as in breast cancer. It is further contemplated that such immune response would provide a protective and therapeutic effect in an individual having such pathophysiological conditions. This is particularly beneficial in light of concerns regarding the safety, purity, and manufacture of various vaccines.

The composition may be administered in a bacterial host or other routes of administration as are known in the art may be used. The immunogenic composition may comprise an adjuvant or a diluent as are standard in the art. The immunogenic compositions may be administered one or more times to achieve an immunogenic effect. It is well within the skill of an artisan to determine dosage or whether a suitable dosage comprises a single administered dose or multiple administered doses.

The following examples are provided for illustrative purposes only and are in no way intended to limit the scope of the present invention:

EXAMPLE 1

Materials and Methods

Mice and Reagents

Female BALB/c mice and NOD.CB17-SCID mice were used (6-8 weeks old; Jackson Laboratory, Bar Harbor, Me.) and housed in the Tulane vivarium. The study was approved by the Tulane Institutional Animal Care Committee. Murine monoclonal antibodies (mAbs) were: CD14, HLA-DR, CD3, CD4, CD8 (Becton Dickinson, Franklin Hills, N.J.); CD62L (Caltag, Burlingame, Calif.); CD86, CD83, and anti-human interferon-γ, IL-2, IL-10, TNF-α (PharMingen, San Diego, Calif.); CD40, HLA-ABC (R&D Systems, Minneapolis, Minn.); CD1a (Dako, Carpentaria, Calif.); CD80, CD83, CD45RA, CD45RO, CD69 (Coulter/Immunotech, Fullerton, Calif.); streptavidin-phycoerythrin (SA-PE); and anti-M13 Ab (Amersham, Piscataway, N.J.).

Other reagents were: lipopolysaccharide, murine GM-CSF, murine IL-4 (Sigma, St. Louis, Mo.), recombinant human GM-CSF (Immunex, Seattle, Wash.) and recombinant human IL-4 (R&D, Minneapolis, Minn.). Complete medium is RPMI1640, heat inactivated 10% fetal calf serum (FCS), 1% L-glutamine, 1% penicillin/streptomycin, 50 μM 2-mercaptoethanol, 1% sodium pyruvate, and 1% essential amino acids (all from GIBCO, NY, N.Y.). The Ph.D.-12™ phage display library was purchased from New England Biolabs (Beverly, Mass.).

Synthesis of Peptides

Peptides were synthesized using 9-fluorenylmethyoxycarbonyl chemistry, purified using by high pressure liquid chromatography to 90% purity and biotinylated by the Auxiliary Biochemistry Core Laboratories, Louisiana State University, New Orleans, La.

Human Cells

Peripheral blood mononuclear cells (PBMCs) were isolated from blood of healthy or HCV+ individuals by Ficoll gradient centrifugation. HCV RNA was detected in the blood of HCV-infected patients by RT-PCR. PBMCs ($10^7$/well) were seeded in 6-well plates for 2 hrs at 37° C. Subsequently, non-adherent cells were removed by several washes using PBS plus 2% fetal calf serum (FCS) and frozen for autologous MLR experiments. Adherent monocytes were cultured with GM-CSF (100 ng/ml) and IL-4 (10 ng/ml) in complete RPMI for 6 days (6). $CD1a^+DR^{bright}$ DC were phenotyped by FACS before use. Rhesus macaque or chimpanzees DC were prepared in a parallel fashion by using Hgm-CSF (100 ng/ml) and Hil-4 (50 ng/ml) for six days (15). Mouse DC were prepared from bone marrow of BALB/c mice as described (16). On day six, $CD11c^+I-A^+$ DC were harvested, phenotyped and used for DC-peptide staining.

Dendritic Cell-Binding Peptides

The Ph.D.-12™ phage display library (17) was panned. Phage ($1.5 \times 10^{11}$) were incubated serially with monocytes, T cells and B cells, then Langerhans DC (7), then MDC, using unbound phage for each subsequent step. MDC-binding phage were eluted with glycine-Hcl (0.2 M, Ph 2.2), neutralized with Tris base (1M, Ph 9.1) and amplified in E. coli. A total of 4 rounds of selection were carried out. EMBL Nucleotide Sequence Database Accession Numbers for peptides #3, #12 and #18 were AJ544526, AJ544527, and AJ544528, respectively.

Fusion of Dendritic Cell-Peptides to HCV NS3

The NS3 coding sequence was amplified from an HCV proviral cDNA using PCR (generous gift of Dr. Srikanta Dash, Tulane University, New Orleans). Following restriction digestion, the PCR product was then inserted into compatible sites in plasmid Pet24d (Novagen, Madison, Wis.). The forward primer encoded $NS4A_{21-32}$ peptide and thus was fused at the 5' end of the NS3 coding region to enhance the stability of the protein (18).

To generate the final construct, the $NS4A_{21-32}$-NS3 coding region was ligated to DNA encoding peptide #3 or control peptide, each of which were followed by a vector-encoded C-terminal his6-coding sequence. Both genetic fusions were verified by sequencing using an ABI-377 Automated Sequencer (Applied Biosystems, Foster city, Calif.). Recombinant NS3 fusion proteins were expressed in E. coli BL21 (DE3) following four hours of induction using 1 Mm isopropyl-β-D-thiogalactopyranoside.

Cell-free extracts were generated by sonication, and the recombinant fusion proteins were purified using a Ni-NTA Superflow Column (QIAGEN, Valencia, Calif.). Bacterial endotoxin was subsequently removed using the END-X B15 Endotoxin Removal Affinity Resin (Seikagaku America, Falmouth, Mass.). Protein quantification and purity was assessed by polyacrylamide gel electrophoresis.

Immunoblotting

Immunoblotting of purified recombinant NS3-FP and NS3-Cfp was performed as described previously (7). Gels were transferred onto nitrocellulose membranes. The transferred proteins were detected using anti-NS3 antibody (Novocastra Laboratories Ltd, U.K.) and visualized with the ECL Western blotting detection system (Amersham Pharmacia Biotech, Piscataway, N.J.).

T Cell Proliferation

Purified $CD4^+$ T cells were obtained by depletion of $CD8^+$, $CD19^+$, $CD56^+$, $CD1a^+$ and $CD14^+$ cells using specific bead-conjugated antibodies (Miltenyi, Auburn, Calif.). $CD8^+$ T cells were purified by depleting $CD4^+$ cells in an analogous fashion. Monocyte-derived DC were incubated with immunogens (1 μg/ml) or control for 12 hrs at 37° C. DC were cocultured with T cells ($10^5$/well of a 96-well plate) for four days in complete RPMI 1640 medium+substituting 10% human $AB^+$ serum (Gemini Bio-Products, Woodland, Calif.) for FCS. Cells were pulsed for the last 16 hrs with 0.5 μCi [$^3$H] thymidine/well (New England Nuclear, Brattleboro, Vt.). [$^3$H] thymidine incorporation was measured using a β-counter. Supernatants of cocultures were assayed for cytokines by ELISA (R&D Systems, Minneapolis, Minn.) on day four.

NOD-SCID Mouse Model

Female NOD.CB17-SCID mice were maintained as we previously described (19). PBMCs were obtained from the blood of healthy, HCV− naïve donors. DC ($5 \times 10^5$/mouse), T- and B-cells ($3 \times 10^7$ in 300 μl PBS/mouse) were combined with NS3-FP (5 μg/mouse), NS3-Cfp (5 μg/mouse), or nothing and administrated intraperitoneally three times at five day intervals. Five days after the last immunization, mice were sacrificed, and human cells were recovered from the peritoneum and separated by Ficoll density gradient centrifugation (20). $CD3^+$ T cells were bead-enriched (Miltenyi, Auburn, Calif.), and analyzed by FACS for intracellular cytokines as we described by gating on human $CD3^+$ cells (19,21).

In addition to NOD-SCID mice model, groups of BALB/c mice were immunized with bone marrow derived $CD11c^+IA^+$ DC ($300 \times 10^3$/mouse) plus NS3-FP (1 μg), NS3-Cfp (1 μg) or no supplement and subsequently injected intraperitoneally (I.P) and into the footpads of the BALB/c mice. This immunization was repeated four times at 5 days intervals. Five days after the last immunization mice were sacrificed and subsequently spleen and lymph nodes were isolated. Spleens and lymph nodes of immunized mice were minced and cell suspensions were prepared. Subsequently, splenic $CD4^+$ and $CD8^+$ T cells were purified using magnetic beads. Bone marrow derived DC were then pulsed with NS3 (500 ng/ml) or HIV gp160 (500 ng/ml) for 12 hrs at 37° C. Pulsed DC were extensively washed and cocultured with autologous $CD4^+$ ($50 \times 10^3$/well of a 96-well plate) and $CD8^+$ T cells ($50 \times 10^3$/well of a 96-well plate) for five days. On day five, supernatants of the cocultures were collected for cytokine analysis. [$^3$H] thymidine incorporation was measured using a β-counter.

Flow Cytometry

MDC ($5 \times 10^5$) were incubated with biotinylated peptides (10 µg/ml each) for 1 hr at 4° C. Subsequently, cells were washed, incubated with SA-PE (1:100) for 1 hr, fixed with 0.1% paraformaldehyde and analyzed on a FACSCalibur™ using standard CellQuest software (Becton Dickinson). T cells were analyzed as we described (19). At least $10^4$ gated events/condition were acquired for all analyses.

Confocal Microscopy

DC were cultured in a tissue chamber (Cover glass chambered 8 wells slide, Nunc) for 12 hrs at 37° C. DC were incubated with either biotinylated peptide #3 or with control peptide for 30 min at 37° C. Cells were fixed with 2% paraformaldehyde for 15 min, and subsequently permeabilized with 1% Tx100 in PBS-FSG (fish skin gelatin, Sigma, St. Louis, Mo.) for 15 min. Biotinylated peptides were detected with a 0.1% streptavidin labeled with Alexa 488 (Molecular Probes, Eugene, Oreg.). The nuclei were stained with ToPro-3 (Molecular Probes). Cells were visualized using a Leica (Leica Microsystems, Exton, Pa.) TCS SP2- confocal microscopy (19).

Statistical Analysis

All values were determined as means±standard error (SE). Statistical analysis was conducted by the Student t-test or $X^2$ test as appropriate. Significance was defined as $p<0.05$.

EXAMPLE 2

Generation and Characterization of DC-Binding Peptides

Peptide libraries can be used to derive 12-mer peptides that bind specifically to matrix or cell surface molecules (17,27). Thus, in order to target immunogenic antigen specifically to DC via targeted molecules expressed solely by these cells, a defined phage display peptide library that does not require a priori knowledge of the DC molecule targeted. Thus, small peptides can be derived from a phage display peptide library that specifically bind to their ligands expressed on DC without modulating the phenotype of these cells.

The Ph.D. 12-mer peptide phage display library was screened for peptide ligands that specifically bound to human DC. After four rounds of screening, twenty candidate phages were identified. DC were incubated with individual phages, and analyzed by flow cytometry (FACS). Phage #3, #12 and #18 significantly bound human DC (not shown). Peptide sequences of these three phages were deduced from nucleic acid sequences, and were designated as peptides #3 (FYPSYHSTPQRP; SEQ ID NO: 3), #12 (AYYKTASLAPAE; SEQ ID NO: 12), and #18 (SLSLLTMPGNAS; SEQ ID NO: 18). A 12-mer peptide (EPIHPETTFTNN; SEQ ID NO: 38), which did not bind to DC, was selected from the same panning as a negative control.

Figure 1A:
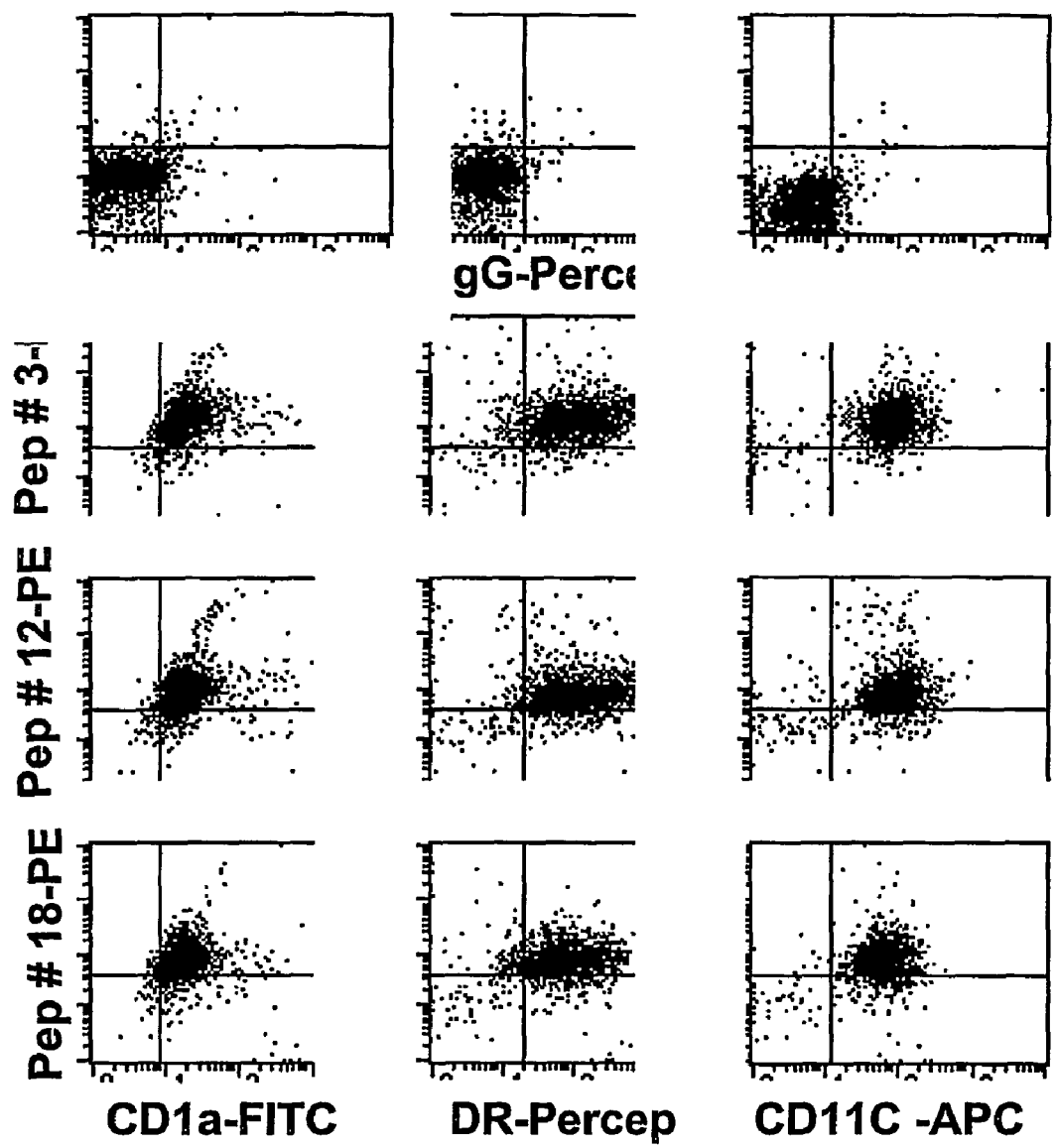
FIGS. 1A-1F shows FACS analysis of DC-binding peptides.
Figure 1B:
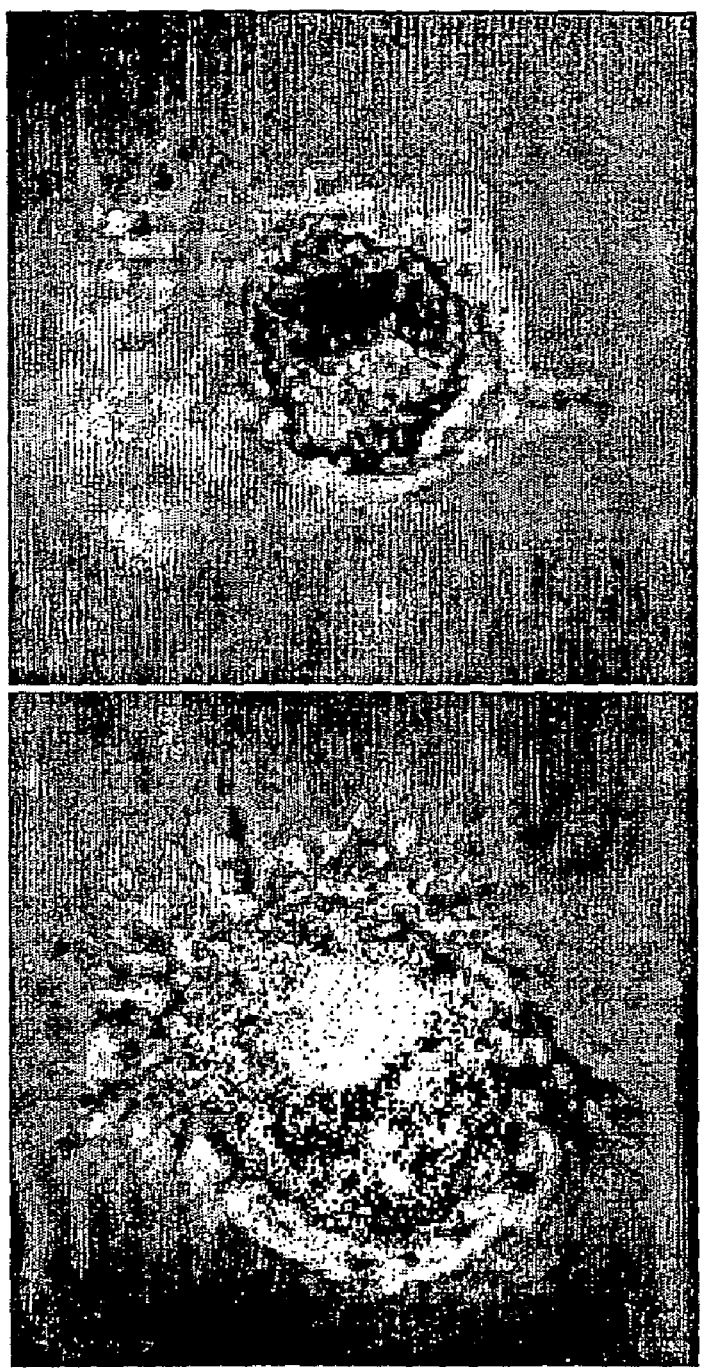
Figure 1C:
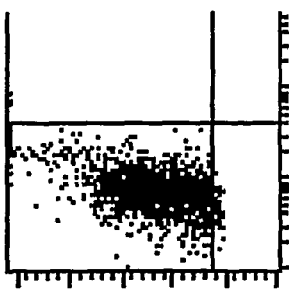
Figure 1C:
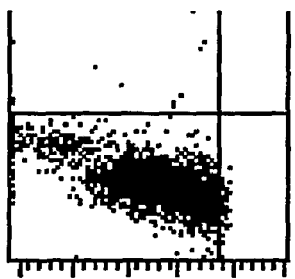
Figure 1C:
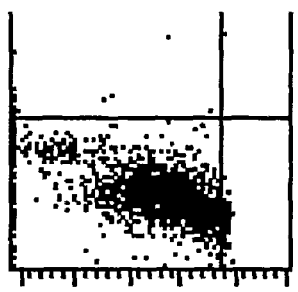
Figure 1C:
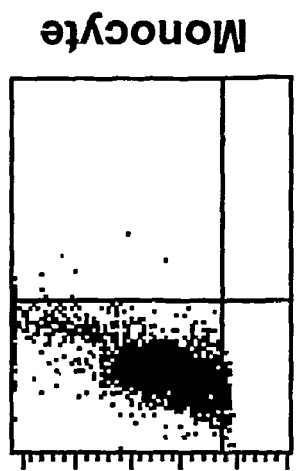
Figure 1D:
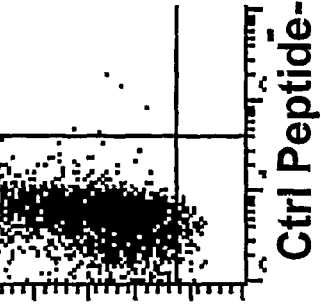
Figure 1D:
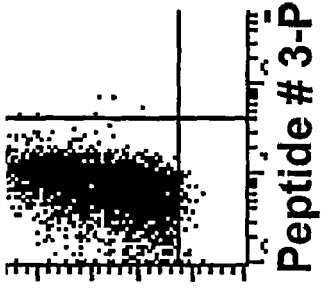
Figure 1D:
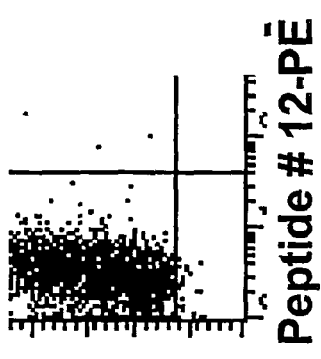
Figure 1D:
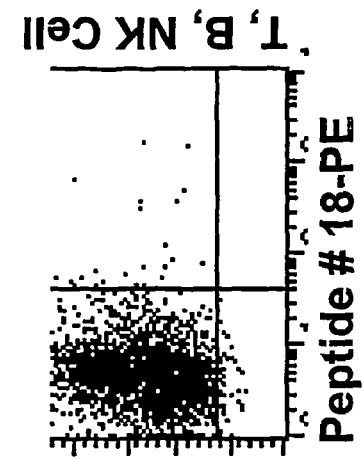
Figure 1F:
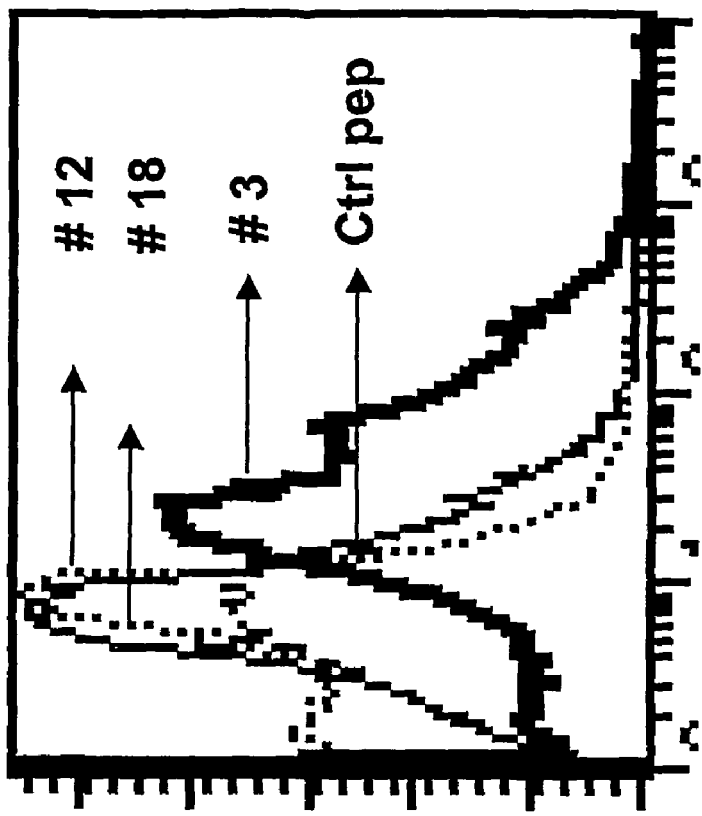
Figure 1E:
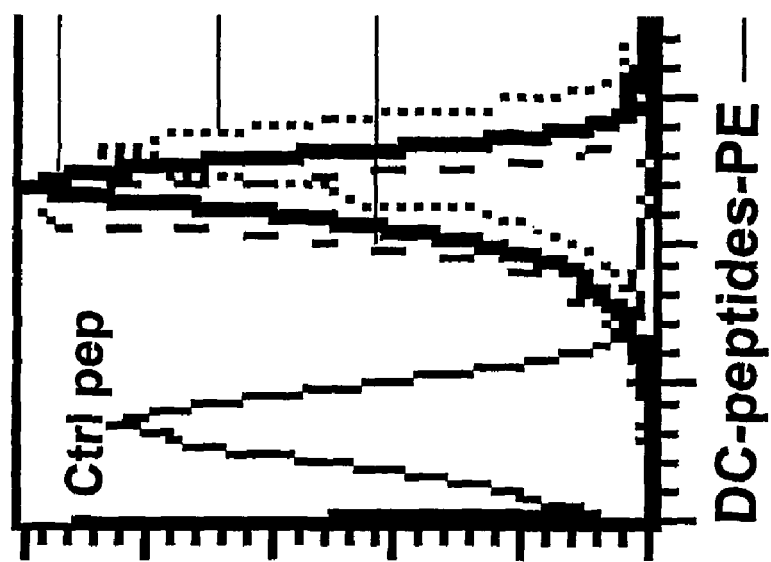

To test peptide binding specificity, biotinylated peptides #3, #12 and #18 were incubated with $CD1a^+DR^{bright}$ $CD11^{bright}$ monocyte-derived human DC, and analyzed by FACS. These peptides bound to DC (FIG. 1A, 1B) but not to monocytes (FIG. 1C) or T-/B-lymphocytes (FIG. 1D). Peptides #3, #12 and #18 all specifically bound to monocyte-derived DC from rhesus macaque (FIG. 1E) or chimpanzee, but not to their T cells, B cells, monocytes, endothelial cells or fibroblasts (not shown). Interestingly, only peptide #3 bound to $CD11c^+I-A^+$ DC derived from mouse bone marrow, where peptide #12 and 18 did not (FIG. 1F).

FACS analyses indicate that DC exhibit bimodal peptide binding capacity, with the majority of these cells binding peptide uniformly, and a small (<5%) subset exhibiting extremely high-level binding. This high-level binding was demonstrated with all three DC-binding peptides, despite the fact that they bind distinct DC epitopes. Thus, it is contemplated that this capacity may be an intrinsic property of these 12-mer peptides. Alternatively, the high-binding subset may represent a unique DC subset.

EXAMPLE 3

Peptides Bind to Distinct and Saturable Sites on DC

Figure 2A:
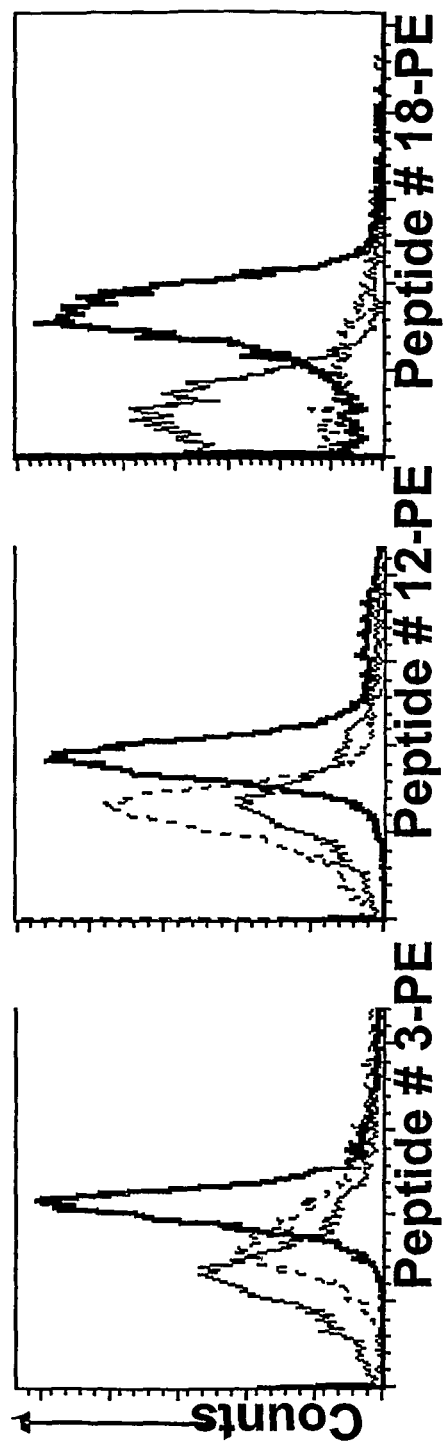
FIGS. 2A-2E demonstrate that peptides bind to distinct and saturable sites on DC.
Figure 2B:
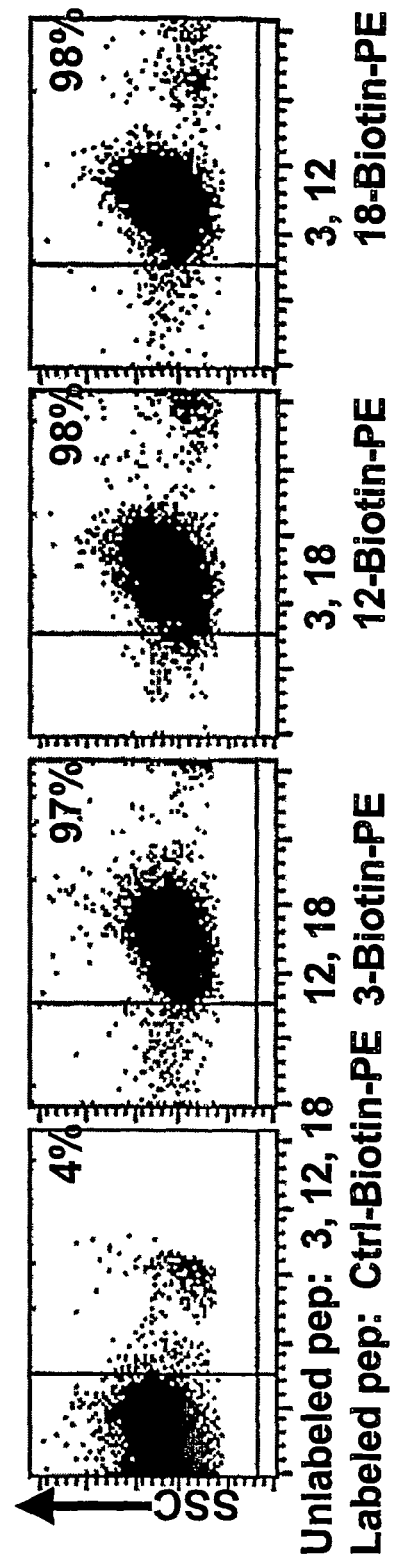
Figure 2C:
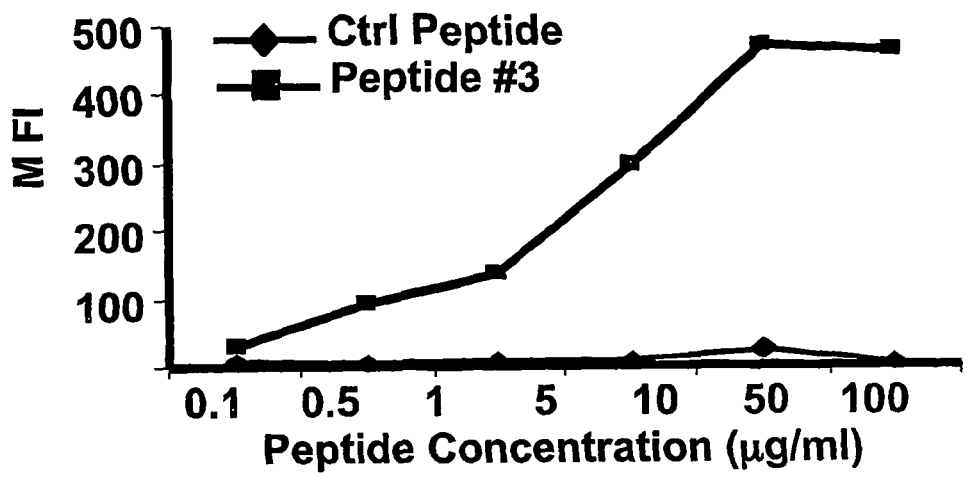

The cognate ligands for these peptides are unknown. Thus, we next tested whether these peptides bound distinct epitopes. DC presaturated with non-biotinylated peptide no longer bound the corresponding biotinylated peptide (FIG. 2A). In contrast, binding of one specific peptide did not inhibit binding of the other two peptides (FIG. 2B). Thus, the three DC-binding peptides bound distinct, saturable DC surface epitopes. The half-maximal relative mean fluorescence of binding for each peptide was reached at a peptide concentration of less than 2 µg/ml (FIG. 2C) suggesting dissociation constants in the nanomolar range.

Figure 2D:
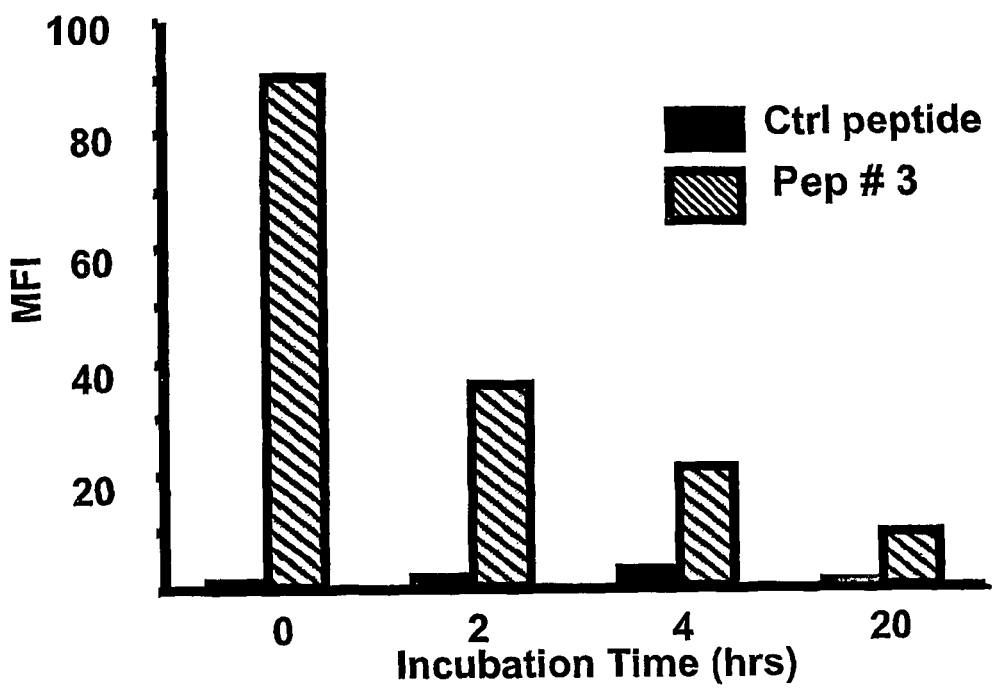
Figure 2E:
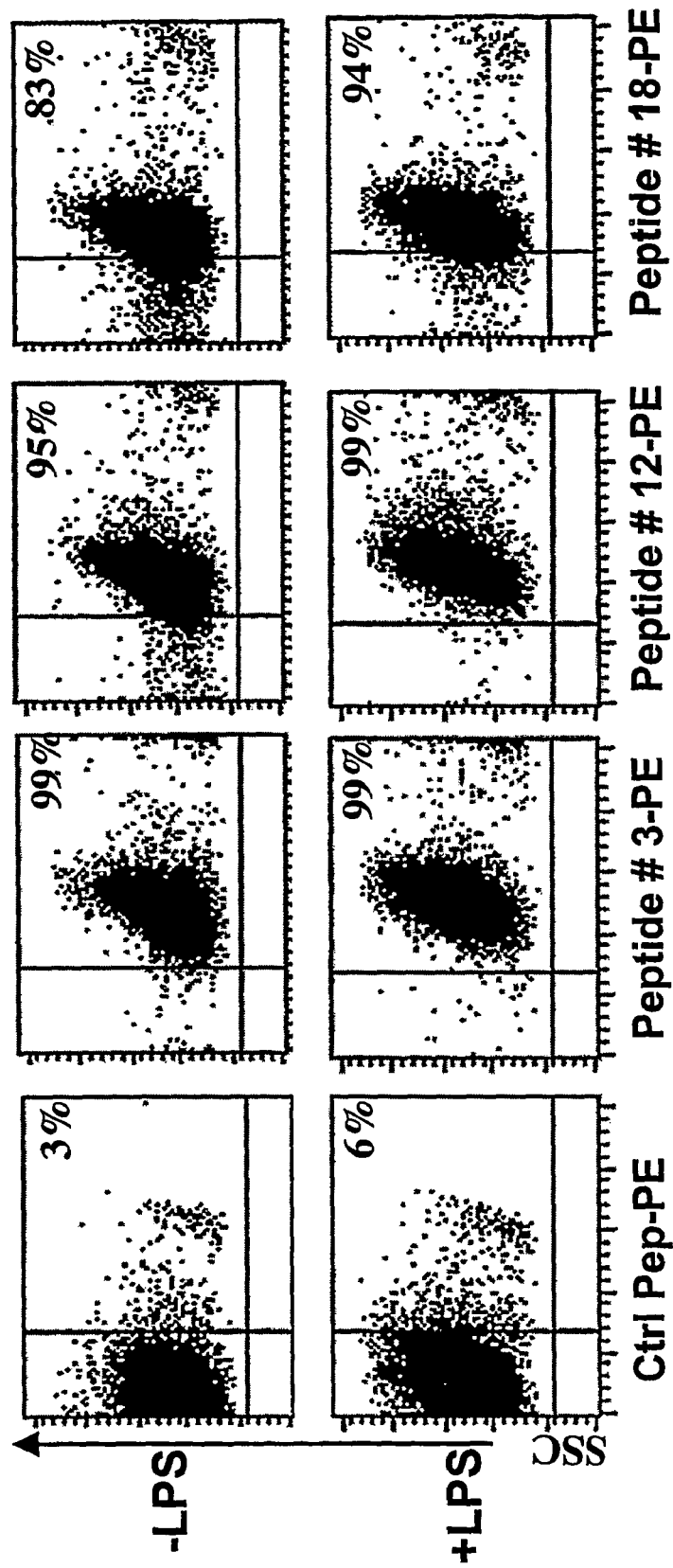
Figure 4A:
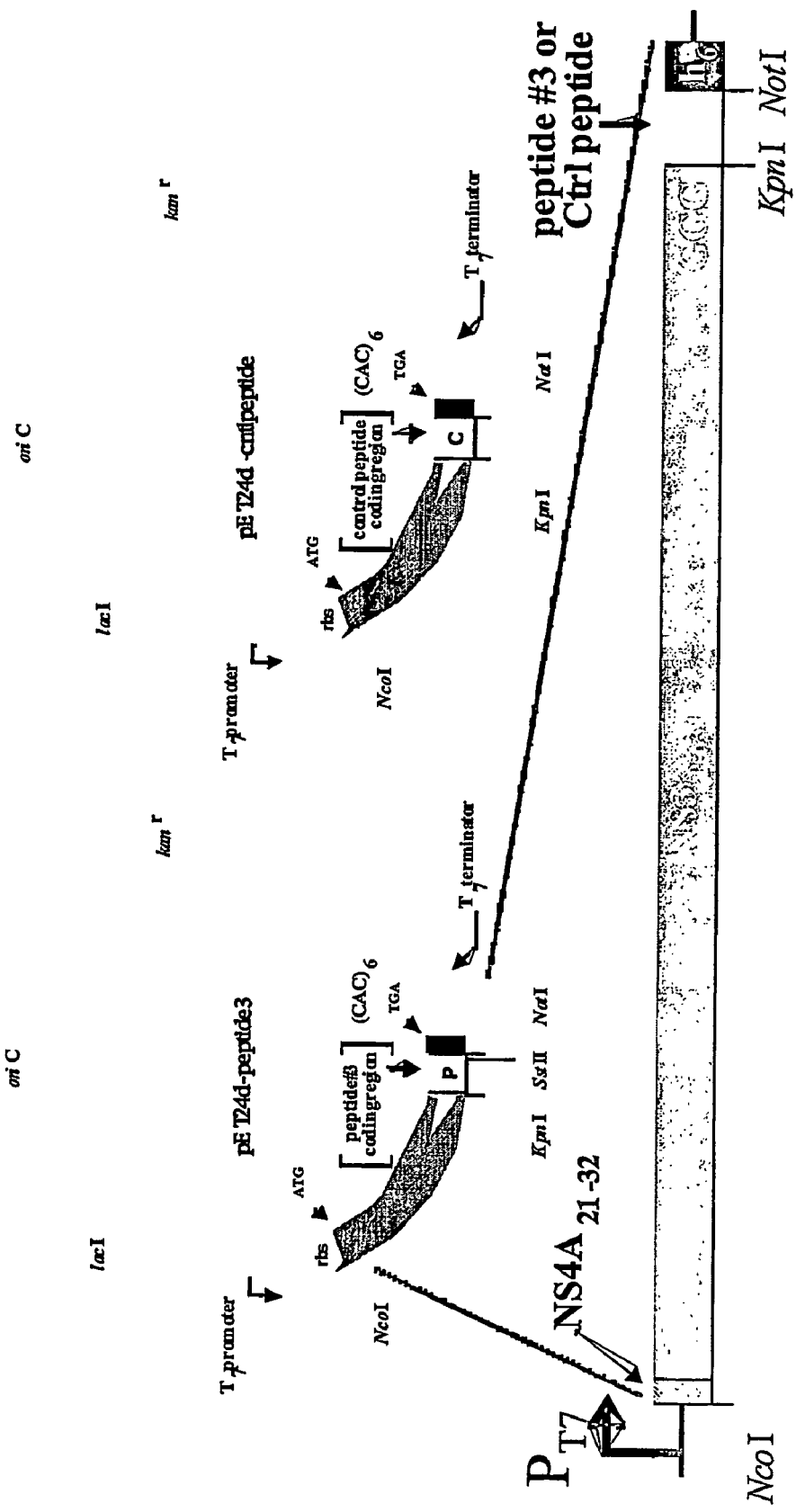
FIG. 4A-4C shows fusion of DC-binding peptide with HCV NS3.
Figure 4B:
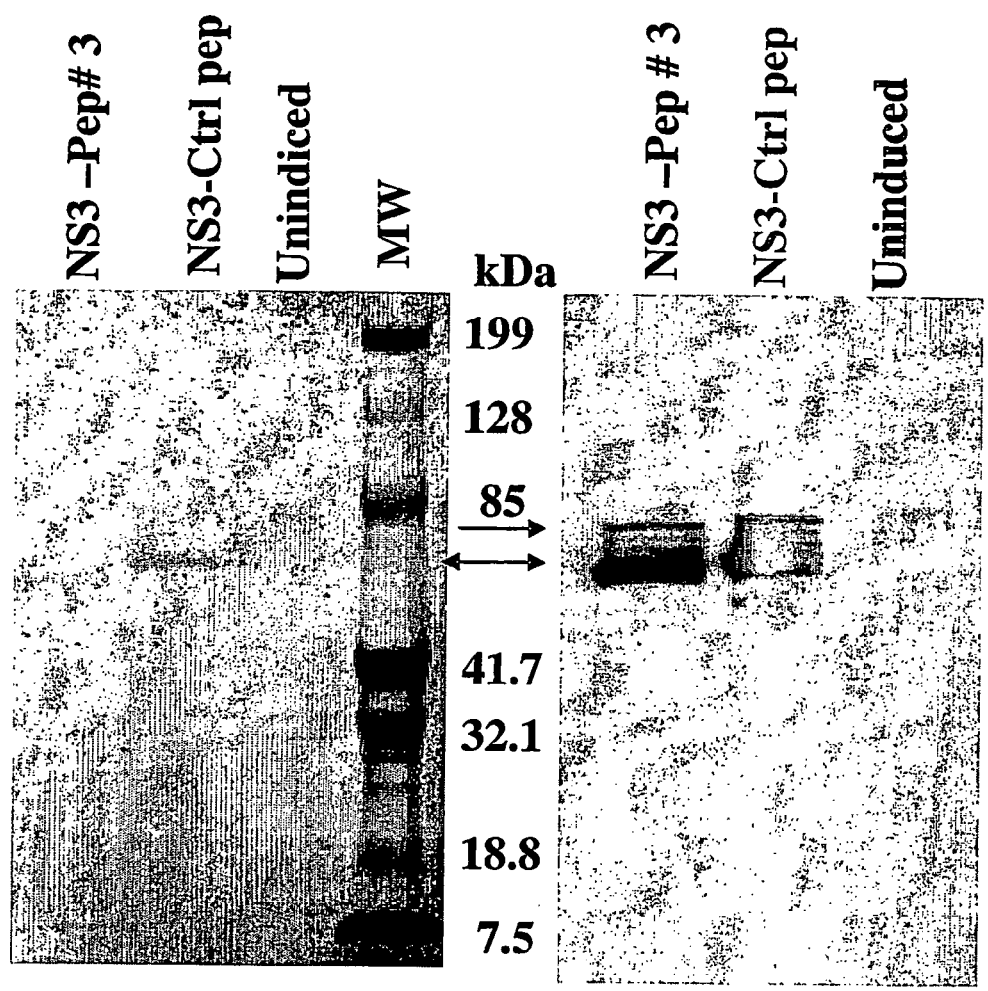
Figure 4C:
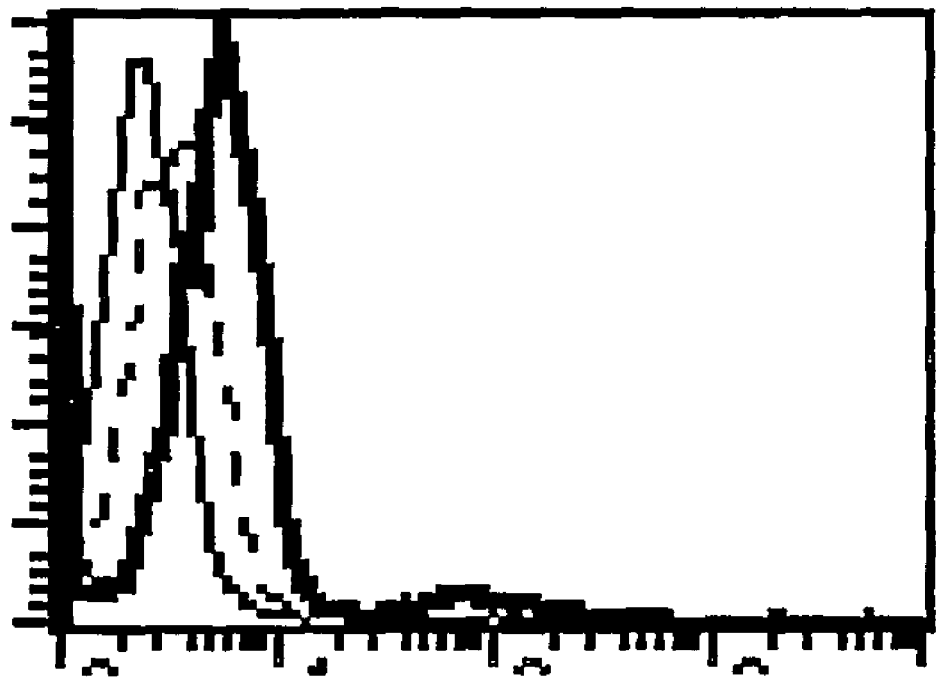

Biotinylated peptide #3 bound immature DC within 1 hr at 4° C. (FIG. 2D). Staining was decreased over the following 20 hrs at 37° C. (FIG. 2D) consistent with antigen uptake by Dcs (15, 22). Importantly, DC remained viable during this period. Peptides bound immature (upper panel) and mature MDC (lower panel) comparably (FIG. 2E), although LPS-mediated maturation appeared to increase peptide binding slightly by inducing a new, minor population of high peptide-binding DC.

EXAMPLE 4

Peptides do not Alter DC Costimulatory Function

To show whether the binding DC-peptides can modulate the phenotype and the accessory functions of DC, human Dcs were treated with synthetic DC-peptides alone and cultured at 37° C. Data show that DC treated with the peptides did not undergo phenotypic or functional changes in order to induce allogeneic $CD4^+$ T cell proliferation and activation (FIG. 3A-3C).

EXAMPLE 5

Genetic Fusion of Dendritic Cell Peptides to NS3 Facilitates DC Capture and Presentation The functionality of DC-binding peptides when NS3 was genetically fused to peptide #3 or control peptide was tested. The coding region of NS3 was fused in frame to DC peptide #3 or control peptide, with a vector-encoded C-terminal histidine tag using Pet24d (FIG. 4A). Following SDS-PAGE and Western blotting, 85 kDa full-length recombinant fusion proteins were detected, along with predominant N-terminally truncated 72 kDa forms (FIG. 4B). As shown in FIG. 4C, the binding of the recombinant NS3-DC peptide #3 fusion protein (NS3-FP) to DC was demonstrated by FACS, and was significantly better than the binding of NS3-control peptide FP(NS3-Cfp).

To demonstrate NS3-FP function, DC were pulsed with NS3-FP, NS3-Cfp, NS3 alone, or nothing, and used to activate autologous $CD4^+$ or $CD8^+$ T cells from HCV-infected individuals. $CD4^+$ and $CD8^+$ T cell proliferation was increased approximately three-fold ($p<0.05$) by incubation of DC with NS3-FP compared to NS3-Cfp, or NS3 alone (FIG. 5A, 5C). Furthermore, $CD4^+$ or $CD8^+$T cells cocultured with NS3-FP-loaded DC became activated and upregulated CD69, CD45RO, and CCR6 (not shown). Interferon-γ and TNF-α production induced by DC treated with NS3-FP was significantly higher ($p<0.05$) than that stimulated by DC pulsed with

Figures 5A, 5B:
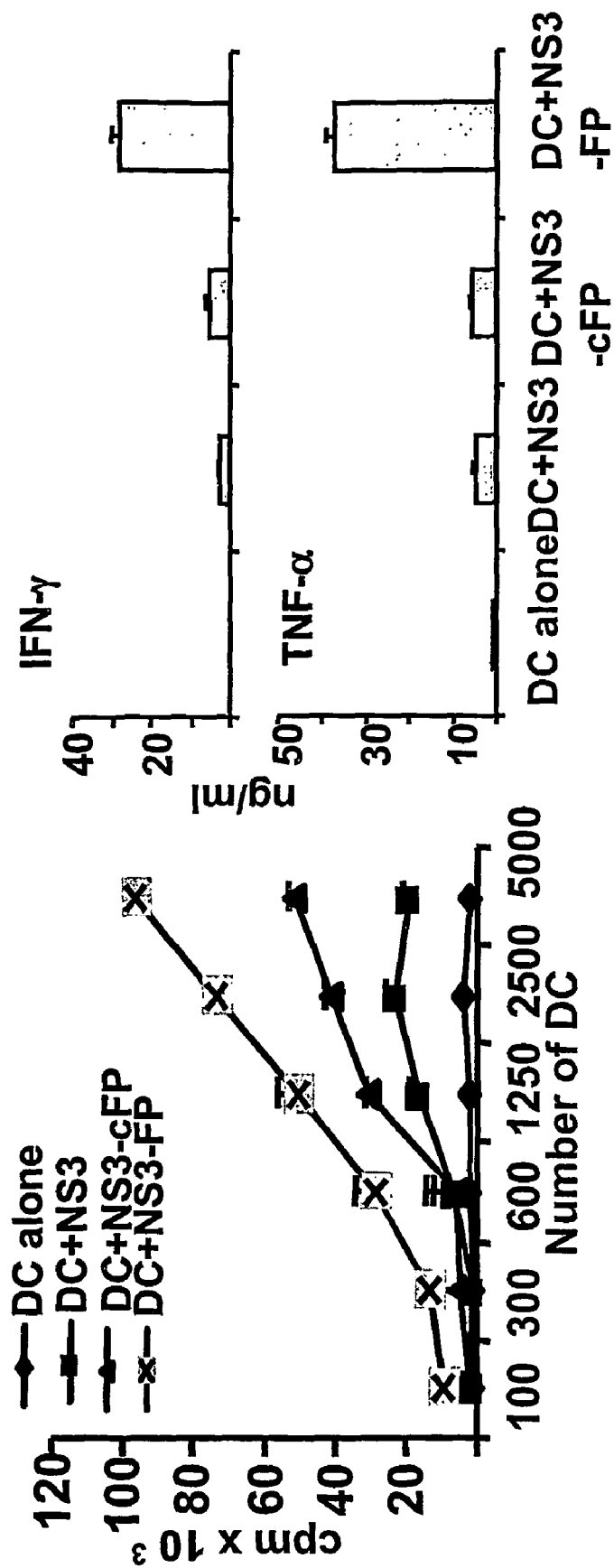
FIGS. 5A-5F demonstrate induction of T cell proliferation and activation by DC charged with NS3-FP in vitro.
Figure 5D:
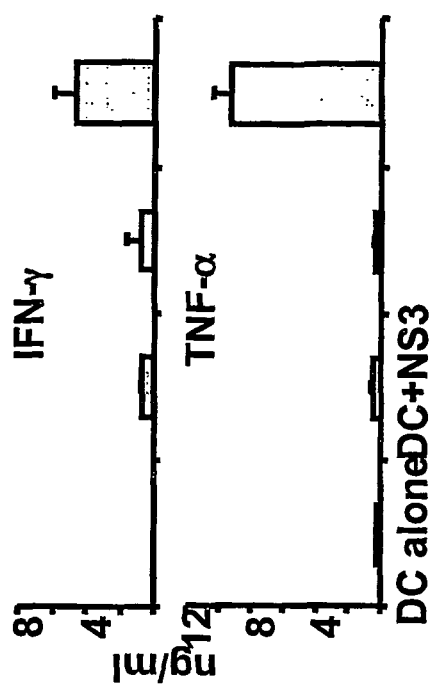
Figure 5C:
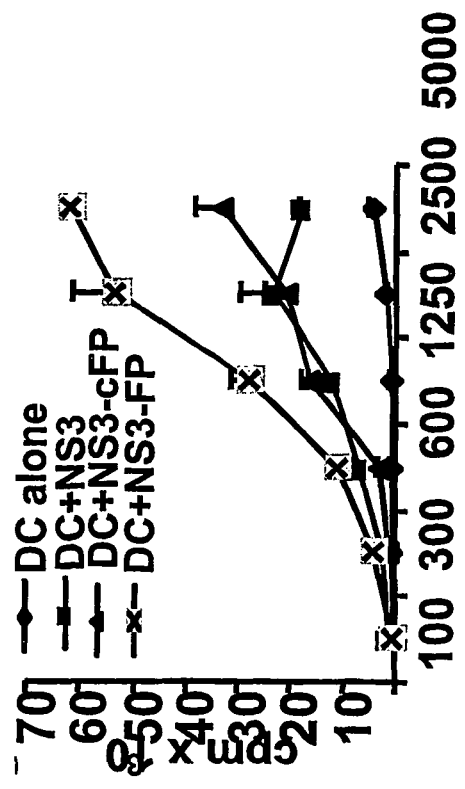
Figure 5E:
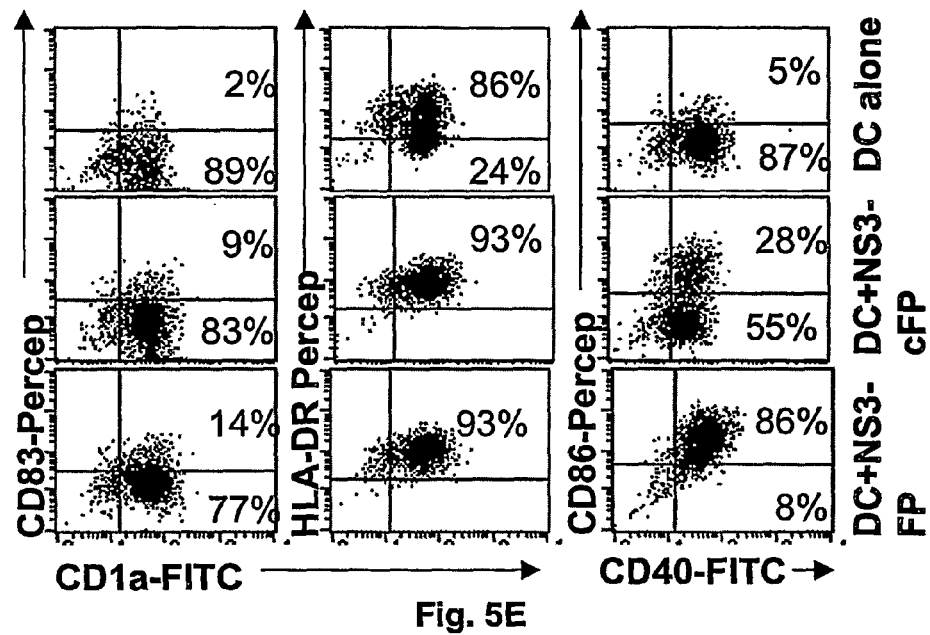
Figure 5F:
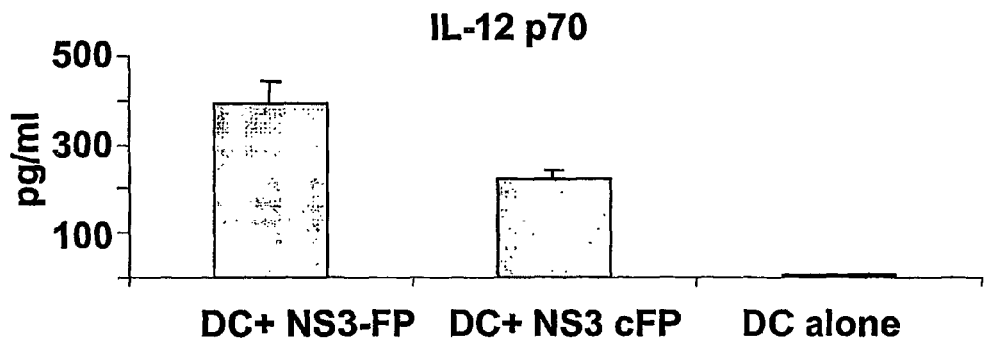

NS3-Cfp or NS3 alone (FIG. 5B, 5D). DC loaded with NS3-FP upregulated CD83, and CD40 and IL-12 p70 higher than NS3-Cfp (FIG. 5E, 5F), suggesting that conjugates do not suppress normal DC function (23).

EXAMPLE 6

In Vivo Studies

To study efficacy of DC-peptides that were genetically fused to NS3 in vivo; we used our NOD-SCID mice model (19). NOD-SCID mice were xenotransplanted with peripheral blood cells, Dcs from HCV negative subjects and the immunogens (NS3-FP, or NS3-Cfp) were administered directly into mice in order to prime naïve T cells in vivo. Vaccinated mice with autologous DC charged with NS3-FP induced significantly more NS3-specific T cell priming as evidenced by NS3-specific cytokine secretion (INF-γ, and TNF-α), CD69 expression and CD4+ T cell proliferation compared to DC pulsed with NS3-Cfp alone (FIG. 6A-6D).

Figure 6A:
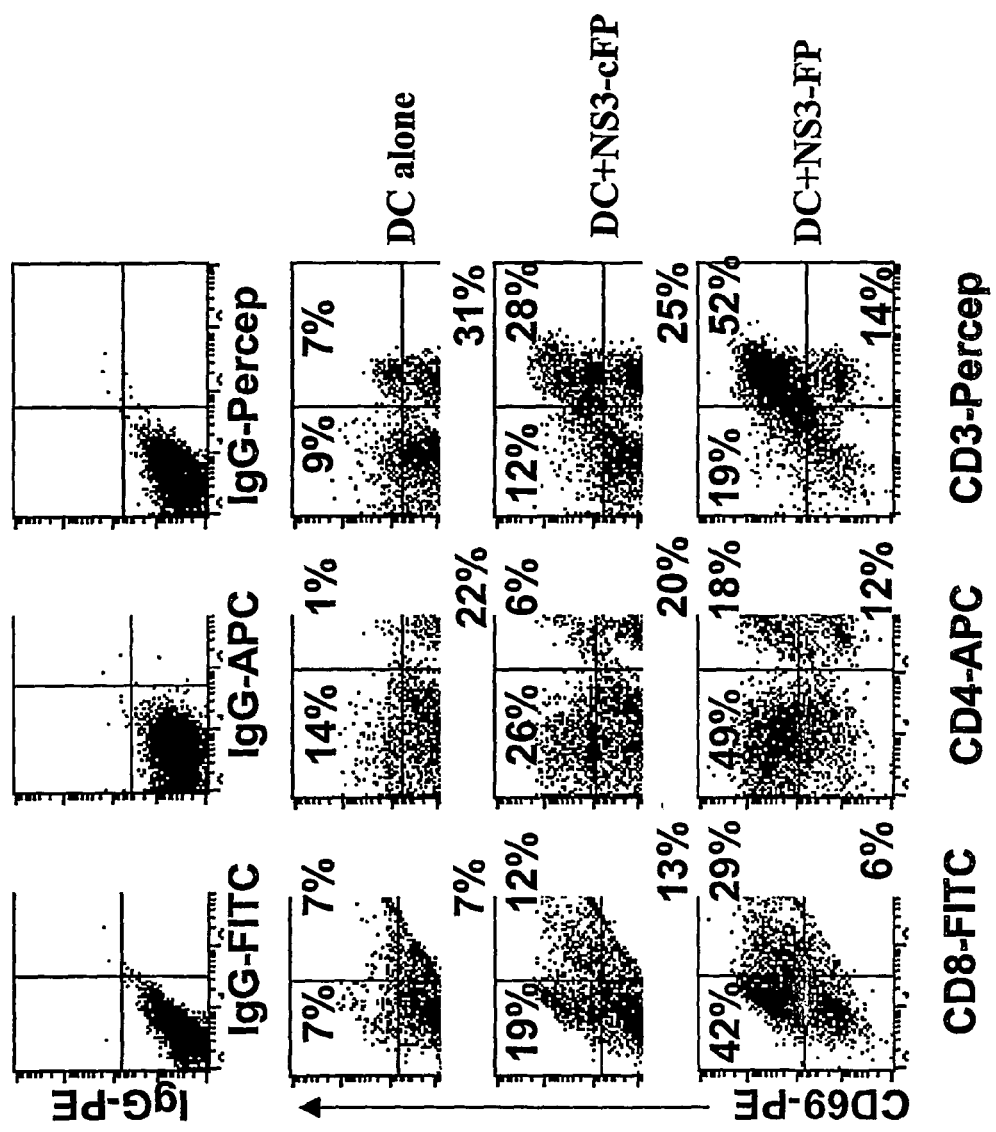
FIGS. 6A-6F show priming of naïve human T cells by DC pulsed with NS3-FP in vivo. Groups of NOD.CB17-SCID mice were immunized with a mixture of human DCs, NS3-FP, NS3-cFP, or with nothing and T and B cells (3×10$^7$/mouse), and injected intraperitoneally into mice. After 3 immunizations at five days intervals, PBMCs were recovered from the peritoneum. T cells of recovered PBMCs were enriched by depleting B-, and NK cells using anti-CD19/CD56 antibodies conjugated with beads.
Figure 6B:
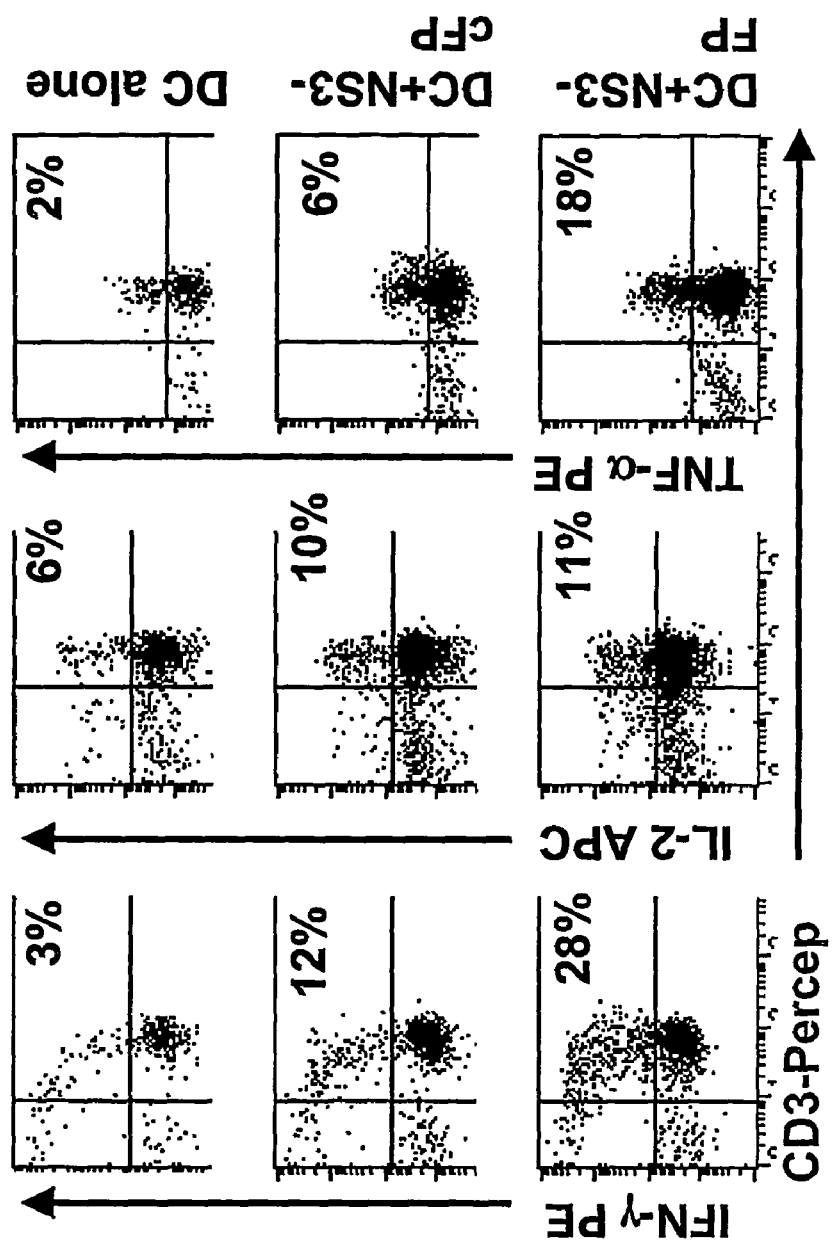
Figure 6C:
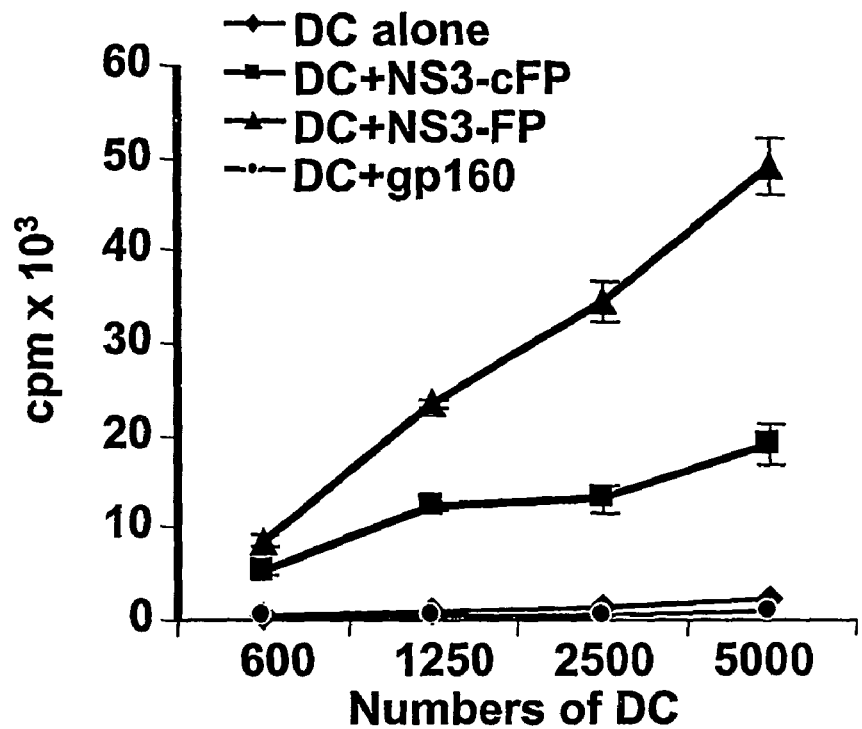
Figure 6D:
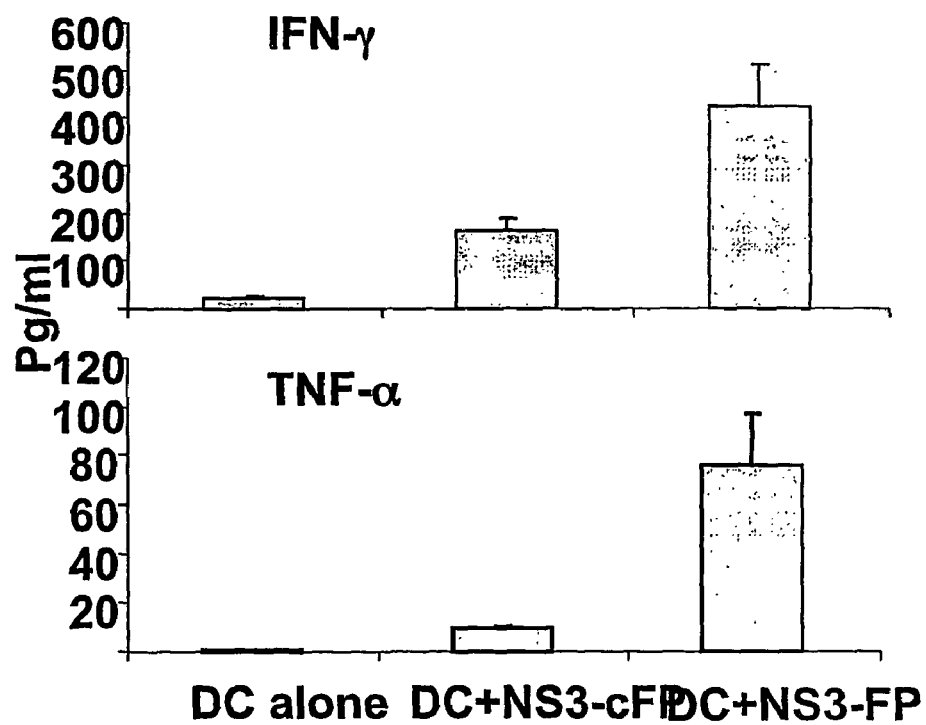
Figure 6E:
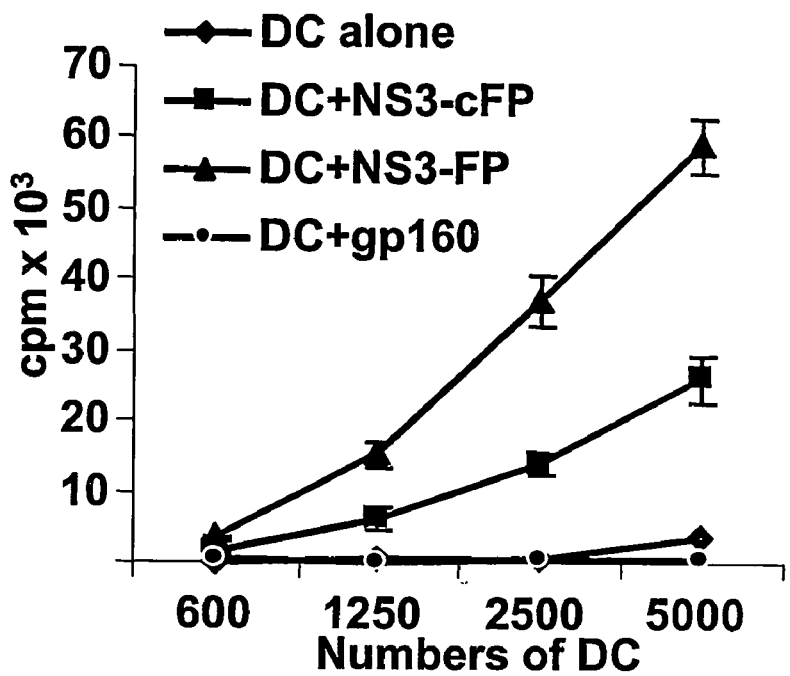
Figure 6F:
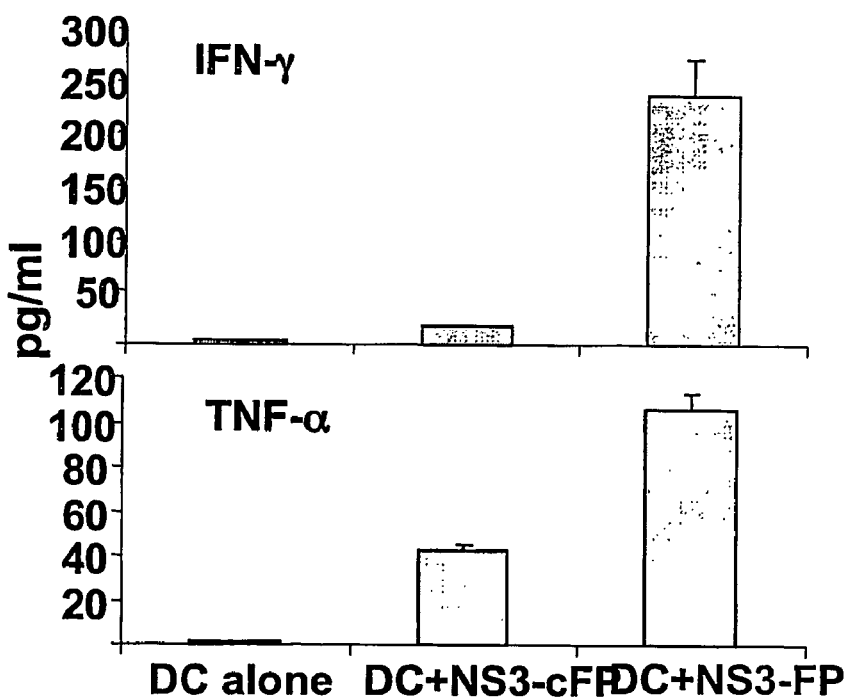

Moreover, significant priming of NS3-specific CD8+ T cells was observed in NS3-FP-vaccinated mice compared with NS3-Cfp vaccinated mice (FIG. 6E, 6F). T cells from mice immunized with NS3-FP or NS3-Cfp did not respond to the control immunogen human immunodeficienby virus (HIV) gp160 suggesting that T cell activation was NS3 specific (FIG. 6C, 6E). Moreover, T cells derived from immunized mice with DC pulsed with NS3-FP compared to DC pulsed with NS3-Cfp enhanced significantly the frequency of HCV-NS3 tetramer positive CD8+ T cells (FIG. 6F).

Figure 7A:
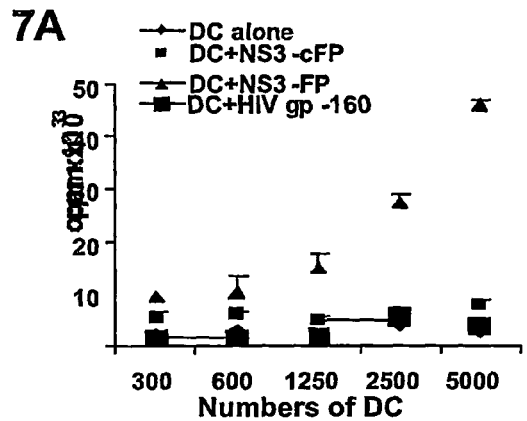
FIG. 7 demonstrates activation of CD4$^+$ and CD8$^+$ T cells by bone marrow DC pulsed with NS3-FP in vivo. Groups of BALB/c mice were immunized with bone marrow DC (300×
Figure 7B:
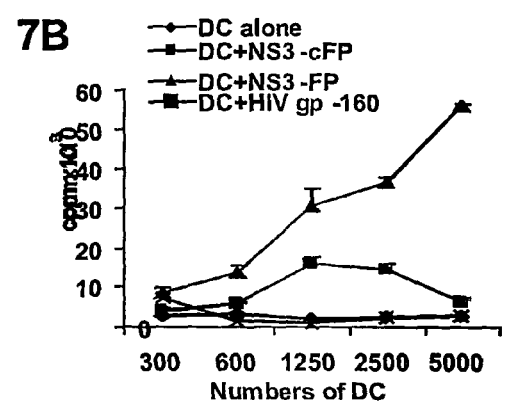
Figure 7C:
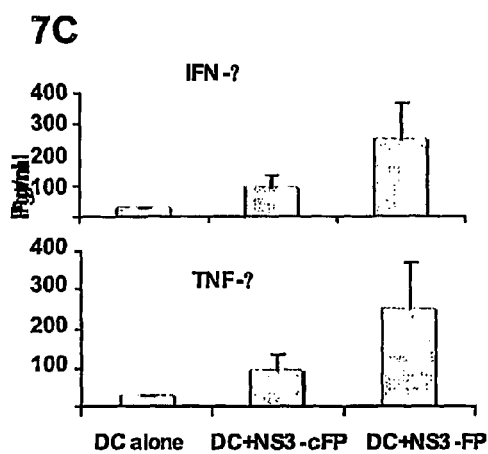
Figure 7D:
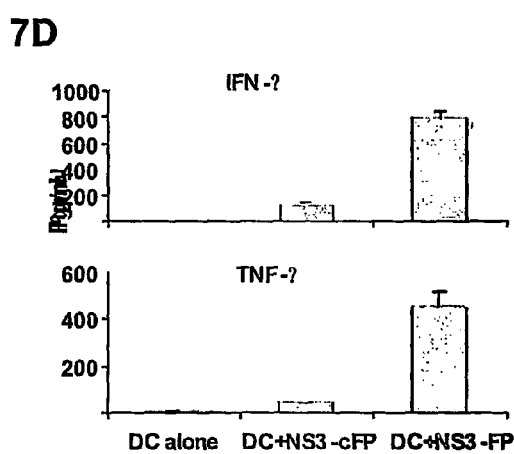

Moreover, in order to further show the efficacy DC-peptide fused to HCV NS3 in vivo, BALB/c mice were immunized with bone marrow derived Dcs pulsed with immunogenic fusions. Data showed that bone marrow derived DC combined with NS3-FP significantly enhanced the expansion of murine CD4+ and CD8+ T cells (FIG. 7A-B) and their subsequent activation (FIG. 7C-D).

EXAMPLE 7

Fusion of HER-2/Neu with DC-Peptides

DNA sequences encoding of peptide # 3 was inserted in-frame between the 3' end of the HER-2/Neu coding sequence and the 5' end of the His6-coding sequence in pET24d. Clones were confirmed by DNA sequencing. The fusion proteins have the following domain organization, HER-2/Neu-DC peptide-His6. By positioning the His-tag to the C-terminus, immediately next to the peptide # 3 or control peptide, purification of truncated forms of the protein lacking the DC-peptide is avoided (FIG. 8A). Recombinant protein was purified by Ni+-affinity chromatography and characterized by mass spectrometry.

DCs were treated with HER-2/Neu-DC peptide #3 fusion protein, or its control, and incubated for 12 hrs at 37° C. to show that the fusion proteins are not toxic and will bind specifically to DCs. The supernatants of treated and untreated DCs were then harvested, and analyzed for IL-12 p70 by an ELISA kit. Data show that the treatment of DCs with HER-2/Neu-DC peptide #3 or with its control were not toxic and after capturing the immunogen, DCs become activated and secreted high levels of 11-12 p70 (19 pg/ml±2.1), and upregulated CD83 and the costimulatory molecules on the cell surface (not shown).

Moreover, in order to show the efficacy of DC targeting strategy, DCs were treated with HER-2/Neu-DC peptide# 3 or its control for 12 hrs at 37° C. These cells were then cocultured with autologous CD4/CD8 T cells for four days. Subsequently, T cell proliferation was measured by [3H] thymidine uptake and T cell activation by cytokine analysis using ELISA. As seen in FIG. 8B, DCs captured HER-2/Neu-DC peptide, processed and presented it to T cells. Moreover, charged DCs induced the activation of T cells clearly toward Th1 responses by secretion of IFN-γ g (FIG. 8C).

EXAMPLE 8

Fusion of HER2/Neu Immunodominant Domain to DC-Peptides

The coding region encompassing all three HER-2/Neu immunodominant domains is created by PCR, and the resulting construct may be verified by sequencing. Primers are directed against the second immunodominant coding region, i.e. epitope 2, with the first and third epitope being encoded by the 5' end of each PCR primer, respectively (FIG. 9A). The resulting amplicon has an N-terminal NcoI site comprising the start codon, and a C-terminal KpnI site to facilitate rapid subcloning into the DC-peptide # 3/control peptide-His6-tagged expression vectors (FIG. 9B).

The fusion proteins have the following domain organization, combined domains of HER-2/Neu-DC peptide #3-His6, or HER-2/Neu-control peptide-His6. Recombinant protein will be purified by Ni++-affinity chromatography and characterized by mass spectrometry. The polypeptide containing the above mentioned features is estimated to be roughly 6-7 kDa. The polypeptide may be characterized by SDS-PAGE and Western blotting using a horseradish peroxidase-conjugated anti-His6 antibody (Invitrogen, Valencia, Calif.).

The following references are cited herein.
1. Banchereau J and Steinman R. Dendritic cells and the control of immunity. *Nature* 392:245 (1998).
2. Cella M, Sallusto F and Lanzavecchia A. Origin, maturation and antigen presenting function of dendritic cells. *Curr. Opin. Immunol.* 9:10 (1997).
3. Caux C, Dezutter-Dambuyant C, Schmitt D, and Banchereau J. GM-CSF and TNFa cooperate in the generation of dendritic Langerhan cells. *Nature* 360:258 (1992).
4. Maraskovsky et al. Dramatic increase in the numbers of functionally mature dendritic cells in Flt3-Ligand treated mice: multiple dendritic cell sub-populations identified. *J. Exp. Med.* 184:1953 (1996).
5. Caux et al. CD34+ hematopoietic progenitors from human cord blood differentiate along two independent dendritic cell pathways in response to GM-CSF+TNFa. *J. Exp. Med.* 184:695 (1996).
6. Sallusto F and Lanzavecchia A. Efficient presentation of soluble antigen by cultured human dendritic cells is maintained by granulocyte/macrophage colony-stimulating factor and downregulated by tumor necrosis factor a. *J. Exp. Med.* 179:1109 (1994).
7. Mohamadzadeh et al. IL-15 skews monocytes differentiation into dendritic cells with features of Langerhans cells. *J. Exp. Med.* 194:1013 (2001).
8. Hsu et al., Vaccination of patients with B-cell lymphoma using autologous antigen pulsed dendritic cells. *Nat. Med.* 2:52 (1996).
9. Nestle et al. Vaccination of melanoma patients with peptide- or tumor lysate-pulsed dendritic cells. *Nat. Med.* 4:328 (1998).
10. Banchereau J, Shuler-Thumer B, Paluka A K, and Schuler G. Dendritic cells as vectors for therapy. *Cell* 106:271 (2001).

11. Diepolder et al. Immunodominant CD4+ T-cell epitope within nonstructural protein 3 in acute hepatitis C virus infection. *J. Virol.* 71:6011 (1997).
12. Tabatabai N M, Bian T H, Rice C M, Yoshizawa K, Gill J, and Eckels D D. Functionally distinct T-cell epitopes within the hepatitis C virus non-structural 3 protein. *Hum. Immunol.* 60:105 (1999).
13. Lin C and Thomson J A. A central region in the hepatitis NS4A protein allows formation of an active NS3-NS4A serine proteinase complex in vivo and in vitro. *J. Virol.* 69:4373 (1995).
14. Eckels D D, Wang H, Bian T H, Tabatabai N, and Gill J C. Immunobiology of hepatitis C virus (HCV) infection: the role of CD4 T cells in HCV infection. *Immunol. Rev.* 174: 90 (2000).
15. Lu W, Wu X, Lu W, and Andrieu J M. Therapeutic dendritic-cell vaccine for simian AIDS. *Nature Medicine* 9:27 (2003).
16. Mohamadzadeh M., Poltorak A N, Bergstresser P R, Beutler B, and Takashima A. Dendritic cells produce macrophage inflammatory protein-1γ, a new member of CC chemokine. *J. Immunol.* 156:3102 (1996).
17. Mummert M, Mohamadzadeh M, Mummert D I, Mizumoto N, and Takashima A. Development of a peptide inhibitor of hyaluronan-mediated leukocyte trafficking. *J. Exp. Med.* 192:769 (2000).
18. Howe et al. A novel recombinant single-chain hepatitis C virus NS3-NS4A protein with improved helicase activity. *Protein Sci.* 8:1332 (1999).
19. Curiel T J, et al. Blockade of B7-H1 improves myeloid dendritic cell-mediated antitumor immunity. *Nat. Med.* 9:562 (2003).
20. Boecher et al. Induction of strong hepatitis B virus (HBV) specific T helper cell and cytotoxic T lymphocyte responses by therapeutic vaccination in the trimera mouse model of chronic HBV infection. *Eur. J. Immunol.* 31:2071 (2001).
21. Zou et al. Stromal-derived factor-1 in human tumors recruits and alters the function of plasmacytoid precursor dendritic cells. *Nat. Med.* 7:1339 (2001).
22. Mohamadzadeh M, Pavlidou, A Enk A, Knop J, Ruede E, and Gradehandt G. Freshly isolated mouse 4F7+ splenic dendritic cells process and present exogenous antigens to T cells. *Eur. J. Immunol.* 24:3170 (1994).
23. Bonifaz et al. Efficient targeting of protein antigen to dendritic cell receptor DEC-205 in the steady state leads to antigen presentation on major histocompatibility complex class I products and peripheral CD8+ T cell Tolerance. *J. Exp. Med.* 196, 1627 (2003).
24. Curiel T J and Curiel D T Tumor immunotherapy: inching toward the finish line. *J. Clin. Invest.* 109:311-312 (2002).
25. Tillman et al. Maturation of dendritic cells accompanies high-efficiency gene transfer by a CD40-targeted adenoviral vector. *J. Immunol.* 162: 6378 (1999).
26. Turley et al. Transport of peptide-MCH class II complexes in developing dendritic cells. *Science* 288:522 (2000).
27. Arap et al. Steps toward mapping the human vasculature by phage display. *Nat. Med.* 8:121 (2002).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the claims.

What is claimed is:

1. An isolated peptide which specifically targets and binds to a dendritic cell, said peptide consisting of 12 amino acid residues and selected from the group consisting of SEQ ID NOS: 1-37.

2. The isolated peptide of claim 1, wherein said dendritic cell is a myeloid dendritic cell, a Langerhans dendritic cell or a plasmacytoid dendritic cell.

3. The isolated peptide of claim 1, wherein said peptide is selected from the group consisting of SEQ ID NOS: 1-20.

4. The isolated peptide of claim 1, wherein said peptide is selected from the group consisting of SEQ ID NOS: 21-37.

5. A fusion protein, comprising:
a peptide consisting of twelve amino acids fused to a non-dendritic cell protein or fragments thereof, wherein said peptide specifically targets and binds to a dendritic cell and is selected from the group consisting of SEQ ID NOS: 1-37.

6. A vaccine delivery system, comprising:
a peptide of 12 amino acids which specifically targets and binds to dendritic cells, said peptide selected from the group consisting of SEQ ID NOS: 1-37 conjugated or fused to:
a virus specific protein; or
a bacteria specific protein; or
a tumor associated antigen; or
fragments thereof.

7. The vaccine delivery system of claim 6, wherein said dendritic cell is a myeloid dendritic cell, a Langerhans dendritic cell or a plasmacytoid dendritic cell.

8. The vaccine delivery system of claim 6, wherein said peptide is selected from the group consisting of SEQ ID NOS: 1-20.

9. The vaccine delivery system of claim 6, wherein said peptide is selected from the group consisting of SEQ ID NOS: 21-37.

10. The vaccine delivery system of claim 6, wherein said system is expressed in a bacterial host and is a fusion of said peptide to a virus specific protein; a bacteria specific protein; a tumor associated antigen; or fragments thereof.

11. The vaccine delivery system of claim 10, wherein said bacterial host is *Salmonella*.

12. A multivalent vaccine delivery system, comprising:
at least two peptides selected from the group consisting of SEQ ID NOS: 1-37 which specifically target and bind to dendritic cells each peptide conjugated or fused to:
a virus specific protein; or
a bacteria specific protein; or
a tumor associated antigen; or
fragments thereof.

* * * * *

UNITED STATES PATENT AND TRADEMARK OFFICE
CERTIFICATE OF CORRECTION

PATENT NO. : 8,372,409 B2  
APPLICATION NO. : 10/552153  
DATED : February 12, 2013  
INVENTOR(S) : Mansour Mohamadzadeh Page 1 of 2

It is certified that error appears in the above-identified patent and that said Letters Patent is hereby corrected as shown below:

<u>On the Title page, Item (57) Abstract,</u>
Line 7, "an immune responses" should read --an immune response--.

<u>In the Specification</u>

<u>Column 2,</u>
Line 44, "MV" should read --HIV--.

<u>Column 4,</u>
Line 29, "and impulsed" should read --and unpulsed--.

<u>Column 6,</u>
Line 48, "is provides" should read --is provided--.

<u>Column 7,</u>
Line 28, "rib ozymes," should read --ribozymes,--.

<u>Column 9,</u>
Line 48, "antigen-presenting Cells are" should read --antigen-presenting cells are--.

<u>Column 10,</u>
Line 31, "AMC" should read --MHC--.

<u>Column 12,</u>
Line 66, "HHNSNERSFHYL" should read --HHNSNHRSFHYL--.

<u>Column 14,</u>
Line 6, "may comprising DNA" should read --may comprise DNA--.

Signed and Sealed this  
Thirtieth Day of July, 2013

Teresa Stanek Rea  
*Acting Director of the United States Patent and Trademark Office*

Column 15,
Line 67, "Foster city," should read --Foster City,--.

Column 17,
Line 54, "CD11$^{bright}$" should read --CD11c$^{bright}$--.

Column 19,
Line 25, "immunodeficienby" should read --immunodeficiency--.
Line 61, "levels of 11-12" should read --levels of IL-12--.

UNITED STATES PATENT AND TRADEMARK OFFICE
CERTIFICATE OF CORRECTION

PATENT NO. : 8,372,409 B2  
APPLICATION NO. : 10/552153  
DATED : February 12, 2013  
INVENTOR(S) : Mansour Mohamadzadeh Page 1 of 1

It is certified that error appears in the above-identified patent and that said Letters Patent is hereby corrected as shown below:

In the Specifications

Column 1,
Line 4, "CROSS-REFERENCE TO RELATED APPLICATIONS

This international application claims benefit of provisional U.S. Ser. No. 60/461,474, filed Apr. 9, 2003.

BACKGROUND OF THE INVENTION"

should read

--CROSS-REFERENCE TO RELATED APPLICATIONS

This international application claims benefit of provisional U.S. Ser. No. 60/461,474, filed Apr. 9, 2003.

This invention was made with government support under Grant No. 5R01AI093370 awarded by National Institutes of Health. The government has certain rights in the invention.

BACKGROUND OF THE INVENTION--.

Signed and Sealed this  
Sixth Day of May, 2014

Michelle K. Lee  
*Deputy Director of the United States Patent and Trademark Office*